United States Patent
Adler, Jr. et al.

(10) Patent No.: US 11,076,776 B2
(45) Date of Patent: *Aug. 3, 2021

(54) APPARATUS AND METHOD FOR REAL-TIME TRACKING OF BONY STRUCTURES

(71) Applicants: Varian Medical Systems, Palo Alto, CA (US); Varian Medical Systems Particle Therapy GmbH, Troisdorf (DE)

(72) Inventors: John R. Adler, Jr., Stanford, CA (US); Ralf Bruder, Lubeck (DE); Floris Ernst, Lubeck (DE); Achim Schweikard, Lubeck (DE)

(73) Assignees: Varian Medical Systems Particle Therapy GmbH, Troisdorf (DE); Varian Medical Systems, Inc., Palo Alto, CA (US)

( * ) Notice: Subject to any disclaimer, the term of this patent is extended or adjusted under 35 U.S.C. 154(b) by 256 days.

This patent is subject to a terminal disclaimer.

(21) Appl. No.: 16/274,039

(22) Filed: Feb. 12, 2019

(65) Prior Publication Data
US 2019/0246954 A1 Aug. 15, 2019

Related U.S. Application Data

(63) Continuation of application No. 14/040,609, filed on Sep. 27, 2013, now Pat. No. 10,201,291.
(Continued)

(51) Int. Cl.
*A61B 5/00* (2006.01)
*A61B 5/107* (2006.01)
(Continued)

(52) U.S. Cl.
CPC .......... *A61B 5/1079* (2013.01); *A61B 5/0035* (2013.01); *A61B 5/0064* (2013.01); *A61B 5/0075* (2013.01); *A61B 5/1075* (2013.01); *A61B 5/441* (2013.01); *A61B 5/4504* (2013.01); *A61B 5/4836* (2013.01); *A61B 5/4887* (2013.01); *A61B 6/5247* (2013.01); *A61B 5/055* (2013.01); *A61B 5/72* (2013.01); *A61B 6/032* (2013.01); *A61B 6/501* (2013.01); *A61B 6/505* (2013.01); *A61B 2090/061* (2016.02)

(58) Field of Classification Search
CPC .................................................. A61B 5/1079
See application file for complete search history.

(56) References Cited

U.S. PATENT DOCUMENTS

| 5,706,821 A | 1/1998 | Mathcer et al. |
| 6,106,464 A | 8/2000 | Bass et al. |
| (Continued) | | |

FOREIGN PATENT DOCUMENTS

KR 101146796 B1 5/2012

*Primary Examiner* — Joseph H Santos Rodriguez

(57) ABSTRACT

A method for measuring skin thickness. The method includes at a first 3D point on an outer surface of a patient, exposing the first point to near infrared (NIR) energy from an NIR source. The method includes measuring reflected energy emanating near the first 3D point, or beam incident point. The method includes determining a pattern of the reflected energy based on a distance from a center of the reflected energy, wherein the center is approximated by the first 3D point. The method includes determining a skin thickness measurement based on the pattern.

19 Claims, 25 Drawing Sheets

Related U.S. Application Data

(60) Provisional application No. 61/719,301, filed on Oct. 26, 2012, provisional application No. 61/798,066, filed on Mar. 15, 2013.

(51) Int. Cl.
*A61B 6/00* (2006.01)
*A61B 6/03* (2006.01)
*A61B 90/00* (2016.01)
*A61B 5/055* (2006.01)

(56) References Cited

U.S. PATENT DOCUMENTS

| | | |
|---|---|---|
| 6,671,542 B2 | 12/2003 | Rennert et al. |
| 7,505,559 B2 | 3/2009 | Kuduvalli |
| 7,720,196 B2 | 5/2010 | Zhang et al. |
| 8,235,530 B2 | 8/2012 | Maad |
| 10,201,291 B2 | 2/2019 | Adler, Jr. et al. |
| 2003/0018271 A1 | 1/2003 | Kimble |
| 2004/0260165 A1 | 12/2004 | Cho et al. |
| 2006/0200017 A1 | 9/2006 | Monfre et al. |
| 2008/0101665 A1 | 5/2008 | Collins et al. |
| 2011/0190637 A1 | 8/2011 | Knobel et al. |
| 2012/0178076 A1 | 7/2012 | Fujita et al. |
| 2013/0006036 A1 | 1/2013 | Raleigh et al. |

APPARATUS AND METHOD FOR REAL-TIME TRACKING OF BONY STRUCTURES

CROSS REFERENCE TO RELATED APPLICATIONS

This application claims priority to and the benefit under 35 U.S.C § 119(c) of U.S. Provisional Patent Application No. 61/719,301, filed on Oct. 26, 2012, entitled "NIR Image Guided Targeting," the disclosure of which is hereby incorporated by reference in its entirety. This application also claims priority to and the benefit under 35 U.S.C § 119(e) of U.S. Provisional Patent Application No. 61/798,066, filed Mar. 15, 2013, entitled "Apparatus and Method for Real-Time Tracking of Bony Structures," the disclosure of which is hereby incorporated by reference in its entirety.

This application is related to U.S. patent application Ser. No. 14/040,604, filed on Oct. 2, 2013, entitled "NIR Image Guided Targeting," now U.S. Pat. No. 9,271,674, the disclosure of which is hereby incorporated by reference in its entirety.

This application is continuation of U.S. patent application Ser. No. 14/040,609, filed on Oct. 2, 2013, entitled "Apparatus and Method for Real-Time Tracking of Bony Structures," now U.S. Pat. No. 10,201,291, the disclosure of which is hereby incorporated by reference in its entirety.

BACKGROUND

Image-guided targeting has a growing role in a range of medical procedures. At its foundation, image-guidance involves the computer correlation of near real time imagery with an historic three-dimensional (3D) volumetric data to determine the spatial location of patient anatomy. That is, image-guided targeting includes techniques and processes that are used to create images of the human body. Typical examples of 3D volumetric data for image-guided targeting include computed tomography (CT) or magnetic resonance imaging (MRI).

The use of this image-guided targeting has been best described for precise localization of patient bony anatomy in 3D space using projection x-rays or cone beam CT. The tacit assumption that underlies most image-guidance is that skeletal anatomy can provide a reliable reference for nearby soft tissue. Nevertheless, sub-millimetric targeting accuracy is possible with such techniques, thereby enabling even the most precise surgical procedures to be performed under image-guidance.

The primary role of x-rays in image-guidance is to define the 3D location of bony anatomy for image-correlation. Their relative capacity to penetrate skin is the cardinal feature of x-rays that enables them to be used for imaging. In contrast, the kilovoltage energy x-rays used in image-guidance are characterized by a much greater proclivity to be scattered off bone, and therefore a much greater likelihood of being blocked from transmission through the tissue being imaged.

Although imaging with x-rays is robust, the challenge of using ionizing radiation burdens this approach because ionizing x-rays are potentially harmful to patients and the medical team. As such, current technologies using ionizing x-rays for image-guidance is rarely done on a continuous basis. For example cone beam CT scans are generally only produced at the start of a several minute to several hour procedure, while projection x-rays used for image correlation are only generated every 20 to 60 sec. The infrequency of such "real time" imaging means that instantaneous patient movement goes undetected, and will result in therapeutic inaccuracies.

Further, in radiosurgery and radiation therapy, tumors are destroyed with a beam of radiation. For instance, methods have been developed in which a mechanical gantry is used to move the beam source. Two x-ray imaging cameras are used to compute the position of the patient's skull during treatment. This x-ray imaging is repeated several times per minute.

However, x-ray imaging in this context has several limitations. Firstly, as previously discussed, x-ray imaging requires ionizing radiation, and is thus invasive for the patient and for the operating team. Radio-surgical procedures may last for up to one hour. Taking x-rays continuously during the entire treatment would expose the patient to a substantial amount of radiation dose from x-ray imaging alone. Secondly, in x-ray imaging it is necessary that the x-ray source be on one side of the patient, and the x-ray detector be one the other side of the patient. Thus sufficient space for placing separate source and detector units is necessary.

What is needed is a truly real time imaging modality that can be correlated to 3D patient anatomy.

SUMMARY

A method for treatment of a patient is disclosed. The method includes determining skin characteristics in a region of a patient. The method includes performing an in-treatment optical scan on a region of the patient, wherein the in-treatment optical scan comprises a near infrared (NIR) energy source. The method includes detecting a plurality of detected signals from the optical scan. The method includes filtering out the skin characteristics from the plurality of detected signals. The method includes determining skeletal anatomy associated with the region from the plurality of signals that is filtered.

In another embodiment, another method for treatment is disclosed. The method includes performing a base scan to obtain relative 3D (three dimensional) positioning of a target within a skeletal anatomy of a patient. The method also includes performing an in-treatment optical scan on the patient to determine 3D positioning of the skeletal anatomy within a treatment system, wherein the in-treatment optical scan comprises a near infrared (NIR) energy source. Further, the operation of performing an in-treatment optical scan includes detecting a plurality of detected signals from the optical scan, and filtering out signaling characteristics for skin of the patient from the plurality of detected signals to obtain signals related to the skeletal anatomy and determine the 3D positioning of the skeletal anatomy. The method also includes registering the 3D positioning of the skeletal anatomy from the in-treatment optical scan and the 3D positioning of the skeletal anatomy determined from the base scan to determine relative positioning of the target within the treatment system.

In another embodiment, a system for providing treatment is disclosed. The system includes a skin detector for determining skin characteristics in a region of a patient. The system also includes an in-treatment near infrared (NIR) optical scanner for performing an in-treatment optical scan on a region of the patient, wherein the in-treatment optical scan comprises a near infrared (NIR) energy source. The system includes at least one detector for detecting a plurality of detected signals from the optical scan. The system includes a filter for filtering out the skin characteristics from the plurality of detected signals. For instance, the filtering mechanism includes an algorithm that computes skin properties based on measurements using statistical information and a per-patient calibration performed from further infrared measurements (e.g., mean skin oxygen saturation, tone, etc.). The system also includes a modeling module for determining skeletal anatomy associated with the region from the plurality of signals that is filtered.

In another embodiment, a method for measuring skin thickness is disclosed. The method includes at a first 3D point on an outer surface of a patient, exposing the first point to near infrared (NIR) energy from an NIR source. The method includes measuring reflected energy emanating near the first 3D point, or beam incident point. The method includes determining a pattern of the reflected energy based on a distance from a center of the reflected energy, wherein the center is approximated by the first 3D point. The method includes determining a skin thickness measurement based on the pattern. Further, the method considers the angle between the incoming laser beam and the skin surface to compensate for measurement errors. The angle is determined from the 3D information of the surrounding 3D points. Further, statistical information about the particular patient (e.g., skin type, color) may also be computed from a full dataset of NIR information or obtained from other sources.

In still another embodiment, a method for treatment is disclosed involving the use of NIR imaging to generate a 3D structure of a skeletal anatomy of a patient. The method includes performing a base scan to obtain relative 3D positioning of skeletal anatomy of an object. The method also includes performing an in-treatment optical scan on the object to determine 3D positioning of a surface of the object, wherein the in-treatment optical scan comprises a near infra-red (NIR) energy source. The method also includes determining a skin thickness based on a pattern of reflected energy caused by the in-treatment optical scan, wherein the skin thickness is determined for each measured point or a subset of points on the surface of the object. The method also includes compensating for a corresponding skin thickness to determine skeletal positioning associated with and underlying a corresponding measured point, the compensation is performed for each measured point on the surface of the object. The method includes determining a 3D positioning of the skeletal anatomy derived from the in-treatment optical scan.

In another embodiment, a system for providing treatment is disclosed. The system includes an in-treatment near infrared (NIR) optical scanner for exposing a first point on an outer surface of a patient to NIR energy. The system includes at least one detector for measuring and/or detecting reflected energy emanating near the first 3D point. The system also includes a pattern generator for determining a pattern of the reflected energy based on a distance from a center of the reflected energy, wherein the center is approximated by the first 3D point. The system also includes a pattern matcher for determining a skin thickness measurement based on the pattern. In one embodiment, a set of numerical values representing photon counts is computed, and a mathematical model is used to compute skin thickness. In particular, a detector is used to capture reflected light of a laser spot. In the case of 2D cameras, the measured intensities/photon counts are accumulated for certain areas to obtain the numerical features. Additional measurement information is collected, such as, the angle between the laser and the surface, the distance to the target, etc. A mathematical model is used to transform measurement and feature data into a skin thickness value.

BRIEF DESCRIPTION OF THE DRAWINGS

The accompanying drawings, which are incorporated in and form a part of this specification and in which like numerals depict like elements, illustrate embodiments of the present disclosure and, together with the description, serve to explain the principles of the disclosure.

DETAILED DESCRIPTION

Figure 1:
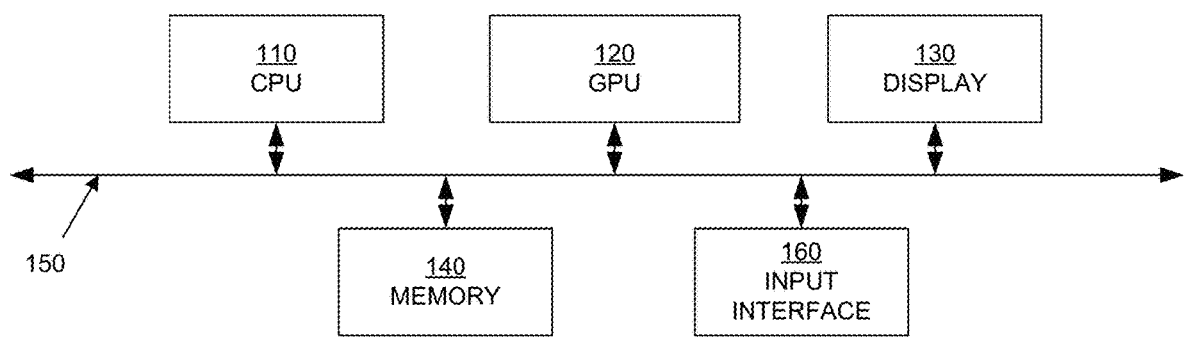
FIG. 1 depicts a block diagram of an exemplary computer system suitable for implementing the present methods, in accordance with one embodiment of the present disclosure.

Reference will now be made in detail to the various embodiments of the present disclosure, examples of which are illustrated in the accompanying drawings. While described in conjunction with these embodiments, it will be understood that they are not intended to limit the disclosure to these embodiments. On the contrary, the disclosure is intended to cover alternatives, modifications and equivalents, which may be included within the spirit and scope of the disclosure as defined by the appended claims. Furthermore, in the following detailed description of the present disclosure, numerous specific details are set forth in order to provide a thorough understanding of the present disclosure. However, it will be understood that the present disclosure may be practiced without these specific details. In other instances, well-known methods, procedures, components, and circuits have not been described in detail so as not to unnecessarily obscure aspects of the present disclosure.

Accordingly, embodiments of the present invention relate to an apparatus for improving the accuracy and efficiency of diagnostic procedures and of surgical procedures. More particular, embodiments of the present invention relate to locating an anatomical target in space. Also, small motions of a patient, either during a medical procedure or during a diagnostic procedure can be compensated, thus allowing for better image quality or more accurate tracking of a target. Other embodiments of the present invention provide for a device that is configured for not using ionizing radiation and not requiring separate source and detector units. Embodiments of the present invention are configured for delivering continuous position information with more than twenty-five (25) images per second over extended periods of time, without harm to the patient.

Some portions of the detailed descriptions that follow are presented in terms of procedures, logic blocks, processing, and other symbolic representations of operations on data bits within a computer memory. These descriptions and representations are the means used by those skilled in the data processing arts to most effectively convey the substance of their work to others skilled in the art. In the present application, a procedure, logic block, process, or the like, is conceived to be a self-consistent sequence of steps or instructions leading to a desired result. The steps are those utilizing physical manipulations of physical quantities. Usually, although not necessarily, these quantities take the form of electrical or magnetic signals capable of being stored, transferred, combined, compared, and otherwise manipulated in a computer system. It has proven convenient at times, principally for reasons of common usage, to refer to these signals as transactions, bits, values, elements, symbols, characters, samples, pixels, or the like.

It should be borne in mind, however, that all of these and similar terms are to be associated with the appropriate physical quantities and are merely convenient labels applied to these quantities. Unless specifically stated otherwise as apparent from the following discussions, it is appreciated that throughout the present disclosure, discussions utilizing terms such as "measuring," "plotting," "matching," "assigning," "performing," "varying," "filtering," "detecting," "determining," or the like, refer to actions and processes of a computer system or similar electronic computing device or processor. The computer system or similar electronic computing device manipulates and transforms data represented as physical (electronic) quantities within the computer system memories, registers or other such information storage, transmission or display devices.

Flowcharts are provided of examples of computer-implemented methods for processing data according to embodiments of the present invention. Although specific steps are disclosed in the flowcharts, such steps are exemplary. That is, embodiments of the present invention are well-suited to performing various other steps or variations of the steps recited in the flowcharts.

Embodiments of the present invention described herein are discussed within the context of hardware-based components configured for monitoring and executing instructions. That is, embodiments of the present invention are implemented within hardware devices of a micro-architecture, and are configured for monitoring for critical stall conditions and performing appropriate clock-gating for purposes of power management.

Other embodiments described herein may be discussed in the general context of computer-executable instructions residing on some form of computer-readable storage medium, such as program modules, executed by one or more computers or other devices. By way of example, and not limitation, computer-readable storage media may comprise non-transitory computer storage media and communication media. Generally, program modules include routines, programs, objects, components, data structures, etc., that perform particular tasks or implement particular abstract data types. The functionality of the program modules may be combined or distributed as desired in various embodiments.

Computer storage media includes volatile and nonvolatile, removable and non-removable media implemented in any method or technology for storage of information such as computer-readable instructions, data structures, program modules or other data. Computer storage media includes, but is not limited to, random access memory (RAM), read only memory (ROM), electrically erasable programmable ROM (EEPROM), flash memory or other memory technology, compact disk ROM (CD-ROM), digital versatile disks (DVDs) or other optical storage, magnetic cassettes, magnetic tape, magnetic disk storage or other magnetic storage devices, or any other medium that can be used to store the desired information and that can accessed to retrieve that information.

Communication media can embody computer-executable instructions, data structures, and program modules, and includes any information delivery media. By way of example, and not limitation, communication media includes wired media such as a wired network or direct-wired connection, and wireless media such as acoustic, radio frequency (RF), infrared and other wireless media. Combinations of any of the above can also be included within the scope of computer-readable media.

FIG. 1 is a block diagram of an example of a computing system 100 capable of implementing embodiments of the present disclosure. Computing system 100 broadly represents any single or multi-processor computing device or system capable of executing computer-readable instructions. Examples of computing system 100 include, without limitation, workstations, laptops, client-side terminals, servers, distributed computing systems, handheld devices, or any other computing system or device. In its most basic configuration, computing system 100 may include at least one processor 110 and a system memory 140.

Both the central processing unit (CPU) 110 and the graphics processing unit (GPU) 120 are coupled to memory 140. System memory 140 generally represents any type or form of volatile or non-volatile storage device or medium capable of storing data and/or other computer-readable instructions. Examples of system memory 140 include, without limitation, RAM, ROM, flash memory, or any other suitable memory device. In the example of FIG. 1, memory 140 is a shared memory, whereby the memory stores instructions and data for both the CPU 110 and the GPU 120. Alternatively, there may be separate memories dedicated to the CPU 110 and the GPU 120, respectively. The memory can include a frame buffer for storing pixel data drives a display screen 130.

The system 100 includes a user interface 160 that, in one implementation, includes an on-screen cursor control device. The user interface may include a keyboard, a mouse, and/or a touch screen device (a touchpad).

CPU 110 and/or GPU 120 generally represent any type or form of processing unit capable of processing data or interpreting and executing instructions. In certain embodiments, processors 110 and/or 120 may receive instructions from a software application or hardware module. These instructions may cause processors 110 and/or 120 to perform the functions of one or more of the example embodiments described and/or illustrated herein. For example, processors 110 and/or 120 may perform and/or be a means for performing, either alone or in combination with other elements, one or more of the monitoring, determining, gating, and detecting, or the like described herein. Processors 110 and/or 120 may also perform and/or be a means for performing any other steps, methods, or processes described and/or illustrated herein.

In some embodiments, the computer-readable medium containing a computer program may be loaded into computing system 100. All or a portion of the computer program stored on the computer-readable medium may then be stored in system memory 140 and/or various portions of storage devices. When executed by processors 110 and/or 120, a computer program loaded into computing system 100 may cause processor 110 and/or 120 to perform and/or be a means for performing the functions of the example embodiments described and/or illustrated herein. Additionally or alternatively, the example embodiments described and/or illustrated herein may be implemented in firmware and/or hardware.

In accordance with one embodiment of the invention, a camera and a projection device are used. The projection device projects light in the visible or infrared range onto the skin surface of a patient. The analysis of the reflection as observed by the camera device is then used to determine the thickness of the skin at the projection spot on the skin surface. In this way, the exact position of the bone at this spatial location can be measured. By repeating this process for a grid of points dispersed over the skin surface, a reconstruction of the bone surface becomes possible. In accordance with the invention, the bone surface can then be used to determine the position of the patient's head, and the position of an anatomical target in space. The derived skeletal scan acts as a surrogate and reference for positions of internal structures.

More specifically, near infrared light is used for image-guided targeting and tracking in embodiments of the present invention. Near infrared (NIR) energy (e.g., light) is defined as a spectrum of electromagnetic energy ranging from about 740 nm to 2000 nm. At these energies, photons have some capacity to pass through modest amount of tissue before being absorbed or exiting the skin surface at some point. Depending on the wavelength used, and the passed tissue properties, photons are absorbed and scattered differently, resulting in different patterns. Different tissues result in a range of intensity patterns formed by the exiting photons on the surface. Absorption increases with increasing wavelength, and scattering decreases with increasing wavelength. The goal is to get as much light into deeper regions with a resulting reflectance, as is described in relation to FIG. 9, wherein a range of optimum wavelengths is determined. Embodiments of the present invention use these properties to localize in 3D space the position of the skeletal anatomy, thereby obviating the need for x-rays.

Other embodiments of the present invention provide for skin characterization, 3D localization of skeletal anatomy of an object and/or patient, and 3D localization of soft tissue targets of an object and/or patient. In particular, in one embodiment, the use of a collimated laser or similar light source (e.g., NIR, etc.) is used to characterize a patient's skin characteristics. In another, the use of NIR is used to visualize the patient's skeletal anatomy using IR reflectance and mapping. It is important that sensitive detectors are used to obtain reflectance readings, in an effort to promote read eye-safe limits (e.g., laser class 1-3).

Still other embodiments of the present invention implement an NIR apparatus. In some implementations, NIR instrumentation for NIR spectroscopy includes a multi-chromatic source, a detector, and a dispersive element (e.g., prism or diffraction grating). As such, scattering/intensity patterns are measured at different wavelengths. In one approach, a white (multi-chromatic) beam is used, such that for every surface point a full such that of spectral information is captured. This information is then displayed as patterns for different wavelengths. In another approach, multiple monochromatic lasers are used one after the other. For each laser, a camera captures the patterns. These approaches allow intensity at different wavelengths to be recorded and sampled either in reflection or transmission mode. Any source for producing NIR radiation may be used. Detectors are sensitive to the range of wavelengths used, and include charge-coupled device image sensors, complimentary metal-oxide-semiconductor (CMOS) based sensors, phosphorous based IR-visible converters, InGaAs photodiodes, etc., taken alone or in combination. These sensors are used to record NIR spectra.

Some embodiments of the present invention are particularly applicable to an apparatus and a method for tracking structures in radiosurgery. It will be appreciated however, that in other embodiments, the apparatus and method have greater utility, such as other types of medical procedures with other types of instruments and other types of imaging devices.

A typical system for radiosurgery is described for better understanding. The system and/or treatment device may include a computer, a beam source and a device for storing a three-dimensional or volumetric image of the patient. For example, a stereotactic radiation treatment device includes a beaming device, which is also called the beam source. This beam source produces a beam of radiation, called the treatment beam. The beam source can be moved to different locations. In this way, the beam can be directed towards the target. Targets are typically tumors, but other lesions can also be treated with this method. In commercially available systems for radiosurgery, the beam source is mounted to a gantry device or a jointed mechanism. This mechanism is programmable, and can move the beam source to appropriate locations in space.

Prior to treatment, a CT or an MR is taken from the region of interest. The target is then marked in the resulting stack of images.

NIR Image Guided Targeting

Figure 2A:
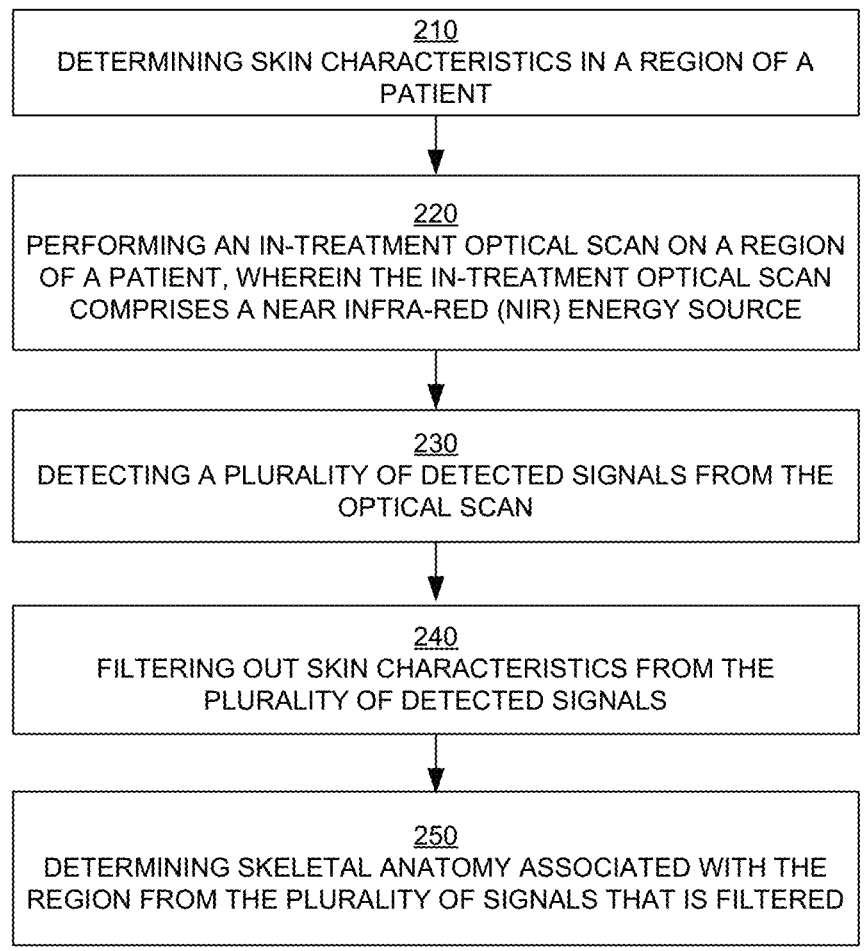
FIG. 2A is a flow diagram 200A illustrating a process for determining skeletal anatomy information of a patient using NIR imaging data, in accordance with one embodiment of the present disclosure.

FIG. 2A is a flow diagram 200A illustrating a process for determining skeletal anatomy information of a patient using NIR imaging data, in accordance with one embodiment of the present disclosure. Some or all of the operations in flow diagram 200A are performed within a computer system including a processor and memory coupled to the processor and having stored therein instructions that, if executed by the computer system cause the system to execute a method for determining skeletal anatomy information of a patient using NIR imaging data. In still another embodiment, instructions for performing a method are stored on a non-transitory computer-readable storage medium having computer-executable instructions for causing a computer system to perform a method for determining skeletal anatomy information of a patient using NIR imaging data. The method outlined in flow diagram 200A is implementable by one or more of the components of the computer system 100 and systems 300A and 300B of FIGS. 3A and 3B, respectively.

At 210, the method includes determining skin characteristics of an object or patient. More specifically, the skin characteristics are determined for a region of a patient. For instance, skin characteristics are determined for a skull region. In other examples, skin characteristics are determined for a region located on a torso of the patient. The region is generally near a surgical target located on or within the patient.

In one embodiment, the skin characteristics are determined by performing an NIR optical scan. For instance, in one embodiment, the use of NIR for the imaging and mapping of a patient's skeletal anatomy involves the characterization of the amount of signal that is absorbed by the patient's skin. This is achieved by using a high intensity laser with a known wavelength and intensity. As such, the use of NIR or other suitable signaling allows for a means of characterizing a patient's external skin characteristics. Also, the use of NIR allows for the means to illuminate the skeletal anatomy in real-time.

For example, when determining skin characteristics, the method includes performing another optical scan on the region of the patient using another source emitting NIR energy. In one embodiment, the source emits energy of varying intensity for a given frequency. In another embodiment the source emits energy of varying frequency. In still another embodiment, the source emits energy of varying intensity and frequency (e.g., wavelength). The method further includes determining signaling characteristics for skin related to at least one of skin reflectance characteristics, skin transmittive characteristics, and a skin fluorescence characteristics, such that the signaling characteristics are filterable from the plurality of detected signals. As such, in one embodiment, the data collected provides a reflectance "spectral cube" which could be assessed for maximal reflectance of underlying anatomy (e.g., through filtering).

In still another embodiment, a higher energy NIR source could be used to elicit excitation of skeletal anatomy and collection of the reflectance signal directly for determining skeletal information (e.g., positioning). Specifically, the method includes performing another optical scan on the patient across varying frequencies and intensity using another NIR energy source. An optimal frequency and intensity combination is determined that optimally illuminates the skeletal anatomy with minimal skin signaling characteristics. As such, the skin characteristics need not be filtered, and as such, the in-treatment optical scan is performed on the patient using the optimal frequency and intensity combination, such that filtering of the skin characteristics are unnecessary.

In another embodiment, the skin characteristics are determined using traditional methods, such as, those performed with using computed tomography (CT) or magnetic resonance imaging (MRI). While true characterization of an individual patient's skin can be carried out by extracting a histological sample of the tissue, it is obviously not conducive for real world clinical treatments in radiation therapy. As such, embodiments of the present invention provide for non-invasive spectroscopic methods to perform skin characterization, to include the following techniques, such as, diffuse reflectance, fluorescence, X-ray fluorescence (XRF) Fourier Transform IR (FTIR), among others.

At 220, the method includes performing an in-treatment optical scan on a region of the patient. The optical scan is performed using an NIR energy source or optical scanner. For example, post skin characterization, in situ visualization of the skeletal anatomy is performed using a broadband, NIR source, and appropriate sensor, as will be described in relation to FIGS. 3B and 3C. The in-treatment optical scan process includes detecting a plurality of detected signals from the optical scan at 230. For instance, the detectors are configurable to receive signals that reflected off the patient, transmittive signals that are transmitted through the patient, and fluorescence signals that are emitted from the patient.

Additionally, at 240, the method includes filtering out skin characteristics for the plurality of detected signals. That is, the data collected at the plurality of detectors is then filtered to remove the contribution from the individual patient's skin that is derived from the characterization step performed at 210. For instance, these calculations can all be carried out on a commercially available GPU based processor providing the capability of real time visualization of skeletal anatomy.

At 250, the method includes determining skeletal anatomy information associated with the region from the plurality of signals that is filtered. In particular, skin characterization increases the accuracy of radiation treatment. That is, the plurality of detected signals can be de-convoluted to remove the contribution from the skin. As such, the underlying skeletal anatomy is obtained.

Figure 2B:
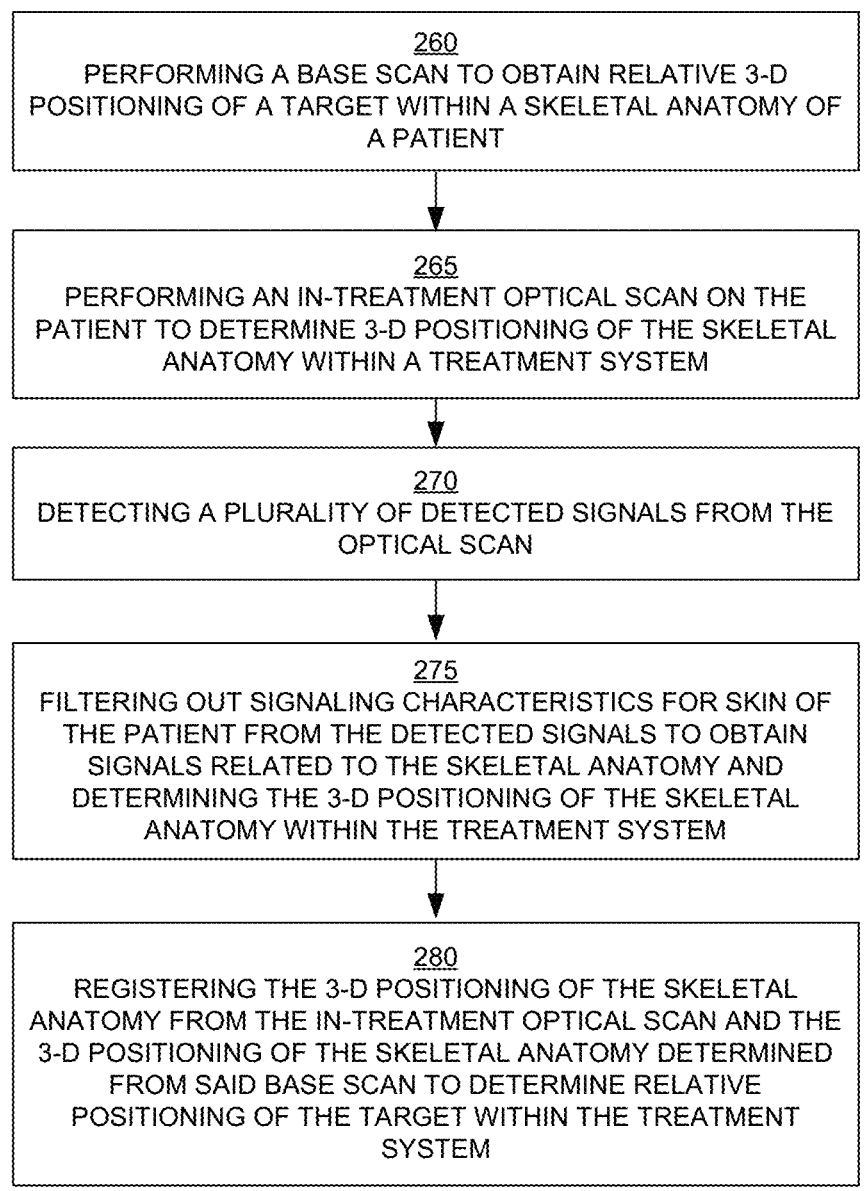
FIG. 2B is a flow diagram 200B illustrating a process for localizing the skeletal anatomy of an object or patient using NIR imaging data, in accordance with one embodiment of the present disclosure.

FIG. 2B is a flow diagram 200B illustrating a process for localizing the skeletal anatomy of an object or patient using NIR imaging data, in accordance with one embodiment of the present disclosure. Some or all of the operations in flow diagram 200B are performed within a computer system including a processor and memory coupled to the processor and having stored therein instructions that, if executed by the computer system cause the system to execute a method for localizing the skeletal anatomy of an object or patient using NIR imaging data. In still another embodiment, instructions for performing a method are stored on a non-transitory computer-readable storage medium having computer-executable instructions for causing a computer system to perform a method for localizing the skeletal anatomy of an object or patient using NIR imaging data. The method outlined in flow diagram 200B is implementable by one or more of the components of the computer system 100 and systems 300A and 300B of FIGS. 3A and 3B, respectively.

At 260, the method includes performing a base scan to obtain relative 3D positioning of a surgical target within a skeletal anatomy of an object or patient. For instance, the base scan includes traditional methodology for performing a planning CT, or MRI. The information obtained from the base scan includes, in part skin characterization information, and skeletal anatomy information.

At 265, the method includes performing an in-treatment optical scan on the patient to determine 3D positioning of the skeletal anatomy within a treatment system or environment. For instance, the method includes illuminating a patient's anatomy with a high intensity NIR source.

At 270, the method includes detecting a plurality of detected signals derived from the optical scan. For instance, the method includes measuring or detecting transmitted, reflected, and fluorescent energy with one or more precisely calibrated sensors/cameras.

At 275, the method includes filtering out signaling characteristics for skin of the patient from the plurality of detected signals to obtain signals related to the skeletal anatomy. In that manner, the 3D positioning of the skeletal anatomy within the treatment system can also be determined. For instance, the method includes using intensity of light and time of flight analysis of the recorded and filtered signal to triangulate and deduce the precise 3D spatial location of the object (e.g., skeletal) surface.

At 280, the method includes co-registering the skeletal model to the reference patient CT or MRI dataset for purposes of accurate patient positioning. Specifically, the method includes registering the 3D positioning of the skeletal anatomy obtained from the in-treatment optical scan and the 3D positioning of the skeletal anatomy determined from the base scan to determine relative positioning of the surgical target within the treatment system. That is, image-to-image correlation is performed, such that the image of the skeletal anatomy is correlated with a prior scan (e.g., CT, MT, or MRI) scan generated through the same object or patient anatomy. The 3D images of the skeletal anatomy scans are compared to determine a closest fit of data. For instance, a least squared comparison process will find the closest fit between the NIR image of anatomy and the previously obtained CT/MRI volumetric data. Thereafter, extrapolation may be performed to determine the 3D spatial location of the surgical target within the object and/or patient. As such, the 3D spatial location of the surgical target is obtained within the treatment system through extrapolation.

Thereafter, once the location of the surgical target is known in relation to the skeletal anatomy, precisely calibrated cameras and appropriate software can then be used to guide stereotactic procedures. That is, the surgical target is then exposed to the treatment beam radiation from the treatment system. Because no ionizing radiation is being used during the localization process, the process of determining skeletal and therefore target position can be continuous, in embodiments of the present invention. That is, the in-treatment optical scan can be performed on the patient on a periodic basis. In one embodiment, the scans are performed 1-5 times per second. In another embodiment, the scans are performed between 20-30 scans per second. Even higher rates are achievable, in other embodiments.

As a result, with continuous patient localization, the method includes updating registration of the 3D positioning of said skeletal anatomy obtained from the in-treatment optical scan and the 3D positioning of the skeletal anatomy determined from the base scan based on a current in-treatment optical scan to determine current relative positioning of the surgical target within the treatment system. As such, the method also includes aligning the target and the treatment beam radiation based on the current relative positioning to expose the target to the treatment beam radiation The accuracy and sensitivity of the various approaches presented in embodiments of the present invention rely may rely on the strength of the reflectance signal received from the skeletal anatomy of interest and on the sensitivity of the detection sensor. In one embodiment, it is advantageous to use a sensor with high spectral and spatial resolution in the NIR spectrum.

Figure 3A:
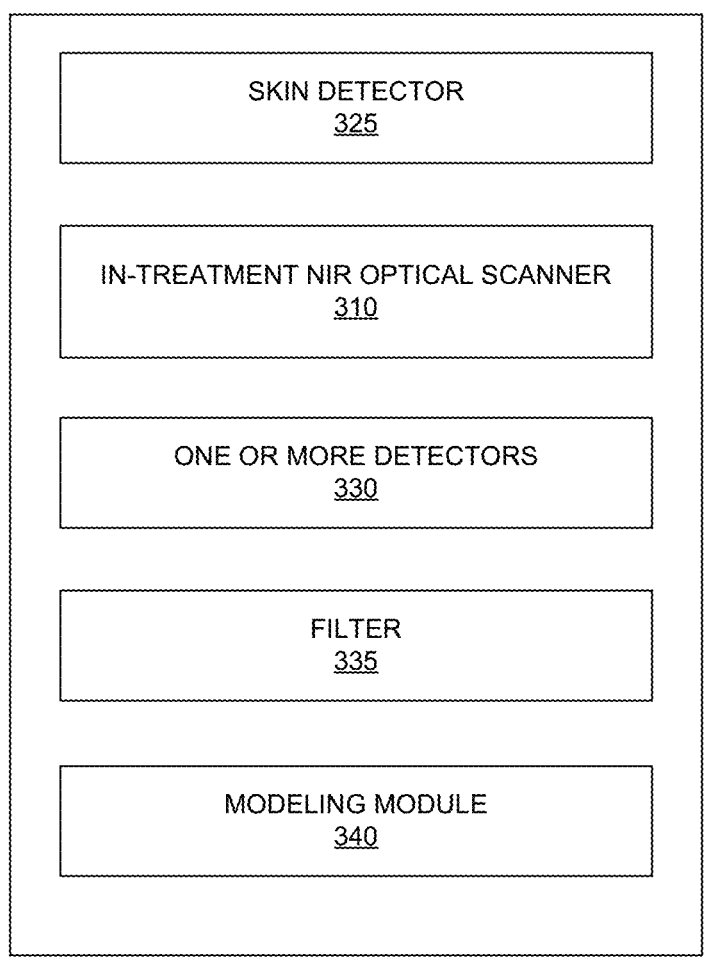
FIG. 3A is a block diagram of a treatment system configured for performing 3D patient modeling through NIR imaging, in accordance with one embodiment of the present disclosure.

FIG. 3A is a block diagram of a treatment system 300A configured for performing 3D patient modeling through NIR imaging, in accordance with one embodiment of the present disclosure. For instance, treatment system 300A is configurable to implement the method of FIG. 2A, and portions of FIG. 2B to provide real-time patient modeling and localization during an in-treatment procedure, in one embodiment. That is, the treatment system 300A is implementable to provide patient modeling and localization in order to provide accurate beam placement on a surgical target within a skeletal anatomy of a patient.

Treatment system 300A includes a skin detector 325 configured for determining skin characteristics of a patient. As previously described, the skin detector may include a traditional CT, MT, or MRI scanning system to determine skin characteristics. In another embodiment, the skin detector 325 may include an NIR optical scanner used to determine customized data related to skin characteristics of a particular patient. For example, signaling related to the skin characteristics may be determinable, and later filtered out to obtain signaling information related to the skeletal anatomy, when the patient is illuminated with NIR energy. For instance, skin detector 325 may perform operation 210 in FIG. 2A, and operation 260 in FIG. 2B, in embodiments.

Treatment system 300A also includes an in-treatment NIR optical scanner 310 configured for performing an in-treatment optical scan on a region of the patient. Information obtained from the optical scanner 310 is used to determine 3D positioning of the skeletal anatomy within a treatment system. For instance, the NIR optical scanner 310 is used to perform operation 220 of FIG. 2A, and 265 of FIG. 2B.

Treatment system 300A also includes one or more detectors 330 configured for measuring and/or detecting one or more of reflected signals, transmitted signals, or fluorescent signals excited and/or derived from the NIR optical scanner 310 after interaction with the patient. For instance, detector 330 is configured to perform operations 230 of FIG. 2A, and 270 of FIG. 2B. Treatment system 300A also includes a filter 335 for filtering out skin characteristics from the plurality of detected signals. For instance, filter 335 is configured to perform operations 240 of FIG. 2A, and 275 of FIG. 2B.

Treatment system 300A also includes a modeling module 340 configured for determining skeletal anatomy of the patient from the filtered and detected signals. In particular, the modeling module 340 models a region of the patient, wherein the region is near to the surgical target. As such, a model of the skeletal anatomy in the region is created by the modeling module 340.

Figure 3B:
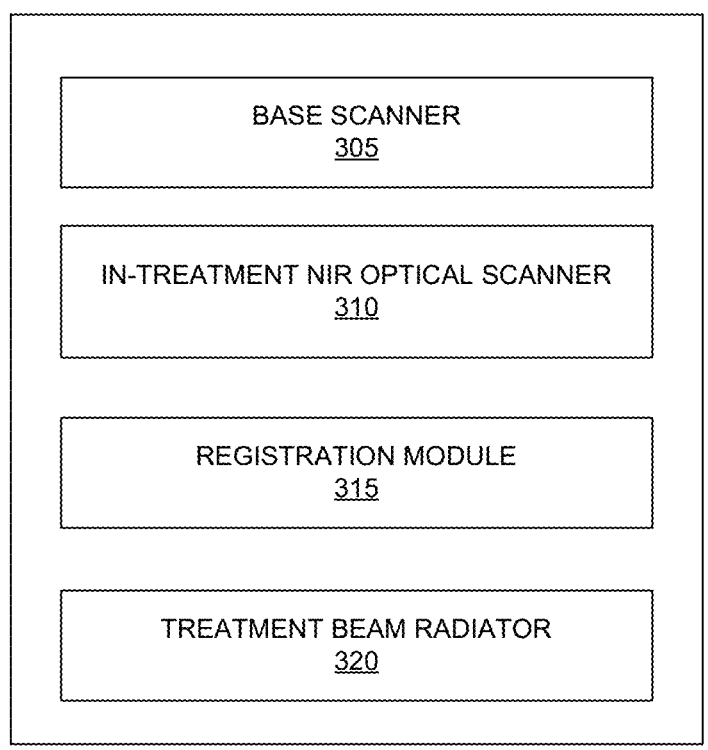
FIG. 3B is a block diagram of a treatment system configured for providing treatment of a patient including in-treatment patient localization determined through NIR imaging, in accordance with one embodiment of the present disclosure.

FIG. 3B is a block diagram of a treatment system 300B configured for providing treatment of a patient including in-treatment patient localization determined through NIR imaging, in accordance with one embodiment of the present disclosure. For instance, treatment system 300B is configurable to implement the method of FIG. 2B, and portions of FIG. 2A to provide real-time patient modeling and localization during an in-treatment procedure, in one embodiment.

As shown, treatment system 300B includes a base scanner 305 configured for performing a base scan to obtain relative 3D positioning of a surgical target within a skeletal anatomy of an object or patient. For instance, base scanner 305 is configured to determine skin characteristics at 210 of FIG. 2A, in one embodiment. Also, base scanner 305 is configured to perform the operation at 260 of FIG. 2B, in one embodiment.

System 300B also includes an in-treatment NIR optical scanner 310 configured to determine 3D positioning of the skeletal anatomy within a treatment system or environment. For instance, scanner 310 is configured to perform an in-treatment optical scan, such as, those operations outlined in 220 of FIG. 2A, and the operations outlined in 265 of FIG. 2B. In that manner, reflected, transmitted, and fluorescent signals are detectable at one or more detectors (not shown) and used for determining a model of the patient. In one embodiment, the skin characteristics are filtered using a filter (not shown) out from the detected signals to obtain a skeletal model of the patient using a modeling module (not shown). For instance, the filtering mechanism includes an algorithm that computes skin properties based on measurements using statistical information and a per-patient calibration performed from further infrared measurements (e.g., mean skin oxygen saturation, tone, etc.).

System 300B also includes a registration model 315 that is configured for registering the 3D positioning of the skeletal anatomy obtained from the in-treatment optical scan and the 3D positioning of the skeletal anatomy determined from the base scan to determine relative positioning of the surgical target within the treatment system. System 300B also includes a treatment beam radiator 320 that is configured for exposing the surgical target to a treatment beam radiation originating from the treatment system.

Figure 3C:
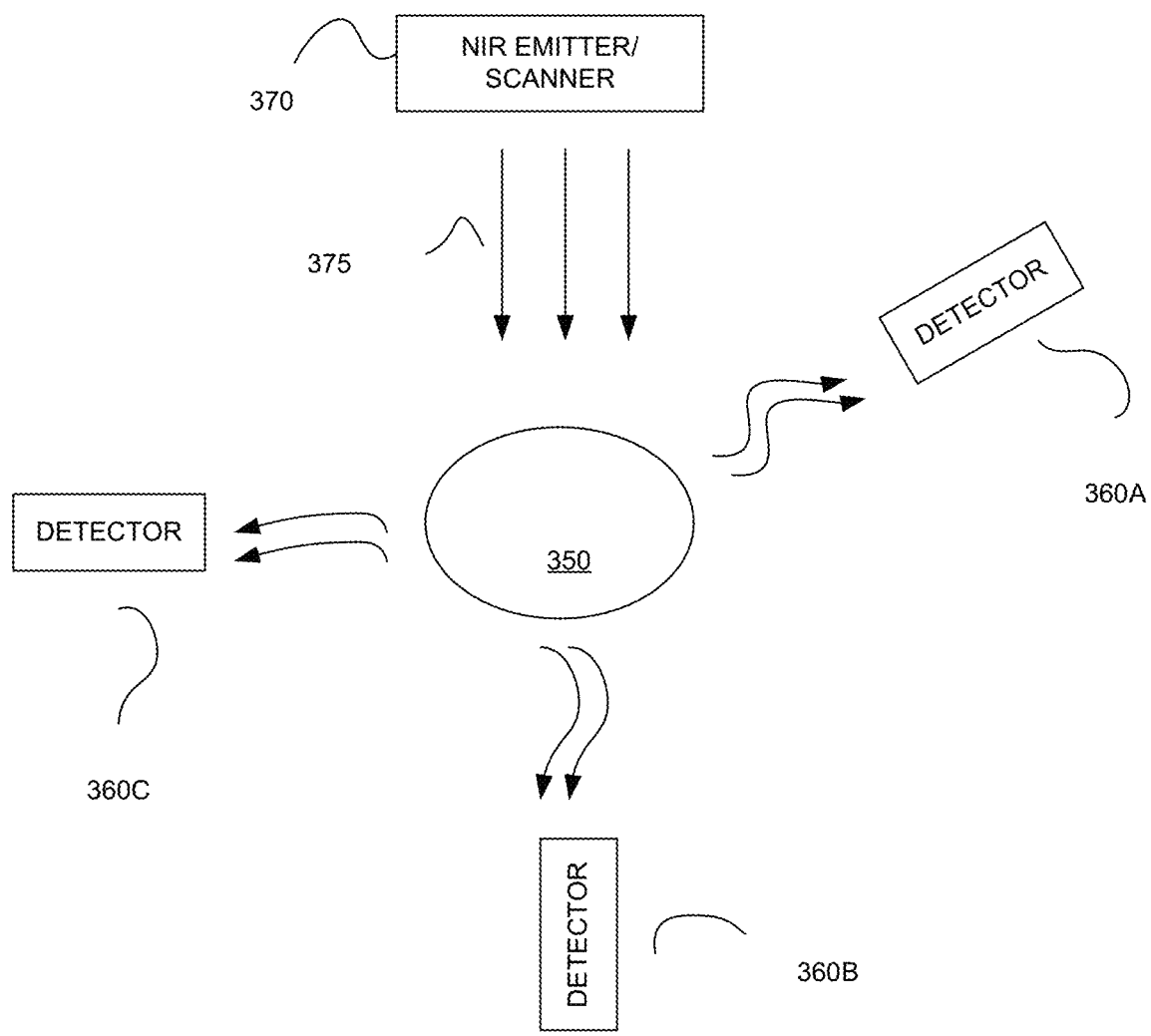
FIG. 3C is an illustration of the application of an NIR imaging system configured for providing 3D patient localization, in accordance with one embodiment of the present disclosure.

FIG. 3C is an illustration of the application of an NIR imaging system 300C configured for providing 3D patient localization, in accordance with one embodiment of the present disclosure. For instance, NIR imaging system 300C is implementable to provide pre-treatment optical scanning used for skin characterization, and in-treatment optical scanning used for determining both in-treatment patient modeling and localization.

In particular, system 300C includes an NIR apparatus as the NIR optical scanner 370 for emitting energy 375 onto an object 350 (e.g., patient). In some implementations, NIR instrumentation for NIR spectroscopy includes a source, a detector, and a dispersive element (e.g., prism or diffraction grating). This allows intensity at different wavelengths to be recorded and sampled either in reflection or transmission mode. Any source for producing NIR radiation may be used.

Detectors 360A-C are sensitive to the range of wavelengths used, and include charge-coupled device image sensors, complimentary metal-oxide-semiconductor (CMOS) based sensors, phosphorous based IR-visible converters, InGaAs photodiodes, etc., taken alone or in combination. These sensors are used to record NIR spectra obtained from reflected, fluorescent, and/or transmitted energy originating from the scanner 370. As an example, detector 360A is used to detect reflected wavelengths or energy, detector 360B is used to detect transmitted wavelengths or energy, and detector 360C is used to detect florescent energy. In embodiments, one or more detectors are use, wherein each detector is configured to detect one or more of the reflected, fluorescent, and/or transmitted energy.

Real-Time Tracking of Bony Structures

Figure 4:
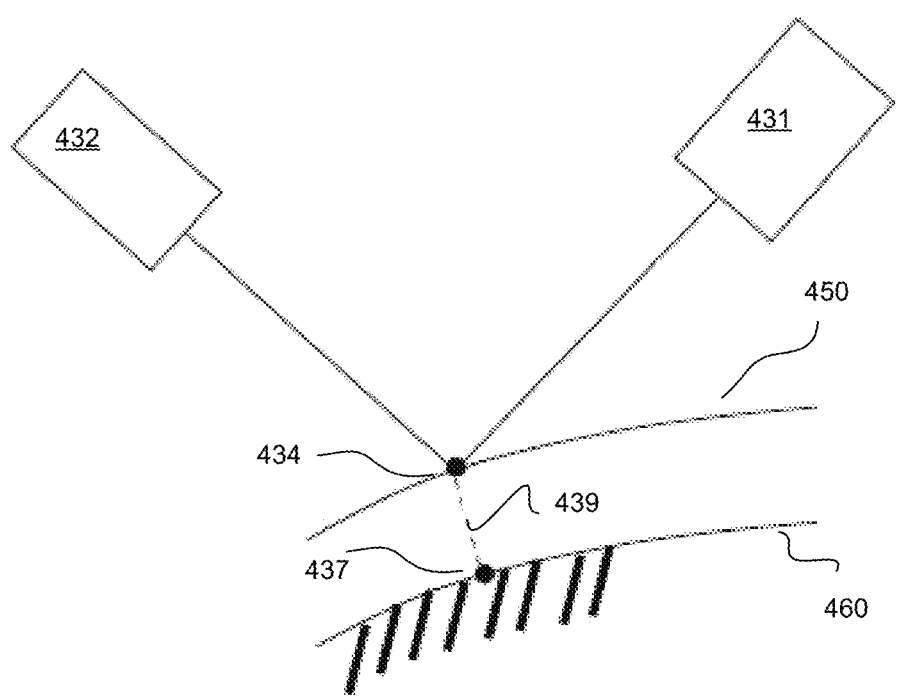
FIG. 4 is a diagram illustrating the measurement of skin thickness, in accordance with one embodiment of the present disclosure.

FIG. 4 is a diagram 400 illustrating the measurement of skin thickness, in accordance with one embodiment of the present disclosure. Measurement of skin thickness is necessary during treatment of a patient, since the target region must be located with high precision. According to embodiments of the present invention, a beam source 432 projects a beam of photons onto the skin surface 450 of a patient. This beam source may be a device for generating a laser beam, or an infrared laser beam or a device for generating a pattern of such laser beams. This beam source is not used to irradiate the target tumor or lesion with a necrotic dose of radiation, but to locate the position of the patient.

The skin surface 450 will reflect the beam to a camera or detector device 431. For example, if the target is in the patient's head, the position of the head must be determined with high precision, and the beam source projects onto the forehead of the patient. According to the invention, the detector or camera device 431 collects photons reflected from the patient.

The thickness 439 of the skin is computed from the patterns of reflection collected at the detector 431. A camera set-up is then used to compute the point 434 in space where the projected photons first reach the skin surface of the patient. The detector and the beam projector are equipped with an internal or external coordinate system. Positions of points in space can be specified with respect to this coordinate system. By adding the distance of the skin from the internal coordinate system and the thickness of the skin at this point of projection, the position of a point 437 on the patient's bone surface 460 can be computed.

By repeating this process, a series of points on the patient's bone surface is obtained. This surface can then be aligned to bone contours extracted from volumetric image data. The volumetric image data may have been obtained from conventional imaging devices such as a CT or MR device. The position of the target with respect to the bone surface is known from the volumetric image data. Overall, the position of the target can be inferred from the repeated measurement of the skin reflection properties and the position of the skin surface.

More specifically, the detector device 431 collects photons reflected after travelling through the skin of the patient and interacting with tissue. To obtain an estimate of the skin thickness at a particular point in accordance with embodiments of the present invention, data on such collected photons is collected which will correlate to the thickness of the skin. This data collection can address any measurement of properties of reflected photons correlating to the thickness of the skin at particular points or areas. Thus according to embodiments of the invention, the correlation measurement can refer to spectroscopy information, phase angle computation of reflected photons, the size, shape and pattern of photon reflection spots, distribution or reflection or intensity patterns, or any other measurement allowing for correlating to skin thickness.

In a preferred embodiment in accordance with the present invention, the detector and the projector are incorporated into a radiation treatment device to report the position of an internal target during the radiation treatment. Because the projector uses non-ionizing radiation during the localization and skin thickness detection process, the process of determining skeletal and therefore target position can be continuous. Additionally, the process of determining skeletal and target position does not interfere with the treatment, such as, MRI.

In a second preferred embodiment according to the present invention, the source and detector are integrated into a surgical or other medical treatment device, so that the method according to the invention provides positioning information on the position of a target internal to the patient. Examples for such medical or surgical treatments are operations in functional neurosurgery, interventions in neurology, or interventions where it is necessary to direct a conventional device for transcranial magnetic stimulation.

In a further embodiment of the invention, the detector and projector are incorporated into a diagnostic device measuring properties of anatomy, such as a conventional MRI or CT or PET or SPECT or ultrasound, magnetic particle imaging, OCT or other medical imaging device. In this embodiment, the source and detector provide alignment information during the data acquisition process, in order to improve the quality of the images obtained. Here the exact information on small motions of the patient during data acquisition allows for compensating such motion, and therefore giving improved quality or resolution of the images. The compact size of the source-detector set-up according to the invention allows for placing the device inside the image acquisition machines where space is limited.

In one embodiment, the computation of position information according to the present invention may be repeated at fixed intervals in time, or it may be applied in a continuous manner so that the information is obtained in real time.

The projection device according to the invention may generate a single beam or a grid of beams at the same time. The grid of beams or the single beam in accordance with the invention may be moved during data acquisition or remain static.

Figure 5:
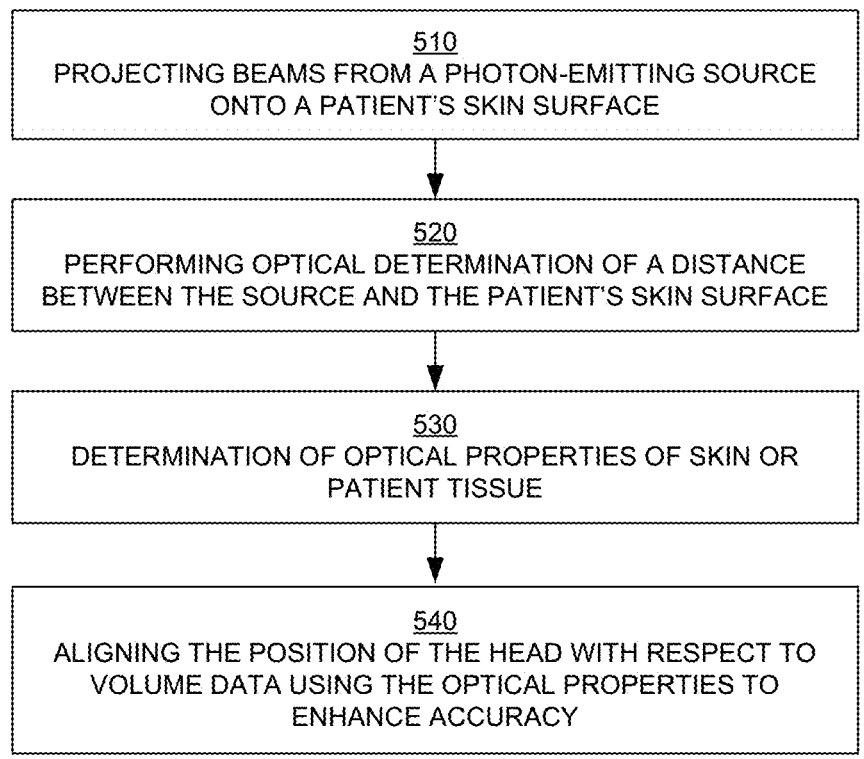
FIG. 5 is a flow diagram illustrating a method for high accuracy patient localization, in accordance with one embodiment of the present disclosure.

FIG. 5 is a flow diagram 500 illustrating a method for high accuracy patient localization, in accordance with one embodiment of the present disclosure. Some or all of the operations in flow diagram 500 are performed within a computing system including a processor and memory coupled to the processor and having stored therein instructions that, if executed by the computer system cause the system to execute a method for localizing the skeletal anatomy of an object or patient using NIR imaging data to high accuracy. In still another embodiment, instructions for performing a method are stored on a non-transitory computer-readable storage medium having computer-executable instructions for causing a computer system to perform a method for localizing the skeletal anatomy of an object or patient using NIR imaging data to high accuracy. The method outlined in flow diagram 500 is implementable by one or more of the components of the computer system 100 and system 600 of FIG. 6.

In particular, at 510, the method includes projecting beams from a photon-emitting source onto a patient's skin surface. At 520, the method includes optically determining a distance between the source and the surface of the patient. At 530, the method includes determining the optical properties of the skin and/or patient soft tissue.

At 540, the method includes aligning the position of the skeletal structure (e.g., cranium or head) with respect to volume data using the optical properties to enhance accuracy. For instance, signals from the skeletal structure are determined from the beam of photons by filtering out the signature of the patient skin. Once the skeletal structure is known, the position of the skeletal structure with respect to a known origin can be determined. Additionally accuracy is achieved by aligning the information of the skeletal structure obtained through the beam energy with bone surface information obtained from CT data, or any other imaging technique. For instance, both point clouds of information including skeletal positioning are registered onto each other.

Additionally, since the beam energy produces non-ionizing energy, continuous exposure to the patient is not harmful, and allows for near real-time or real-time information regarding skeletal positioning. In that manner, over a period of time, the skeletal structure of the patient can be tracked over that same period.

In one embodiment, the position of the skin surface of the patient is calculated. The position of the patient's bone surface is determined by adding skin thickness information obtained from reflection properties. For instance, the skin thickness information or skin signature may be subtracted from the reflected and transmissive information obtained by the beam energy.

In still other embodiments, physical properties of photon reflection such as spectroscopy information, or phase angle information or time-of-flight information or information on the distribution of reflection patterns of reflected photons are measured. A correlation to skin thickness is determined based on the collected information.

In embodiments of the present invention, target localization is used in conjunction with medical imaging to improve image quality or resolution. In other embodiments, target localization is used in a surgical or medical intervention. In still another embodiment, target localization is used in conjunction with a radiation treatment device.

Figure 6:
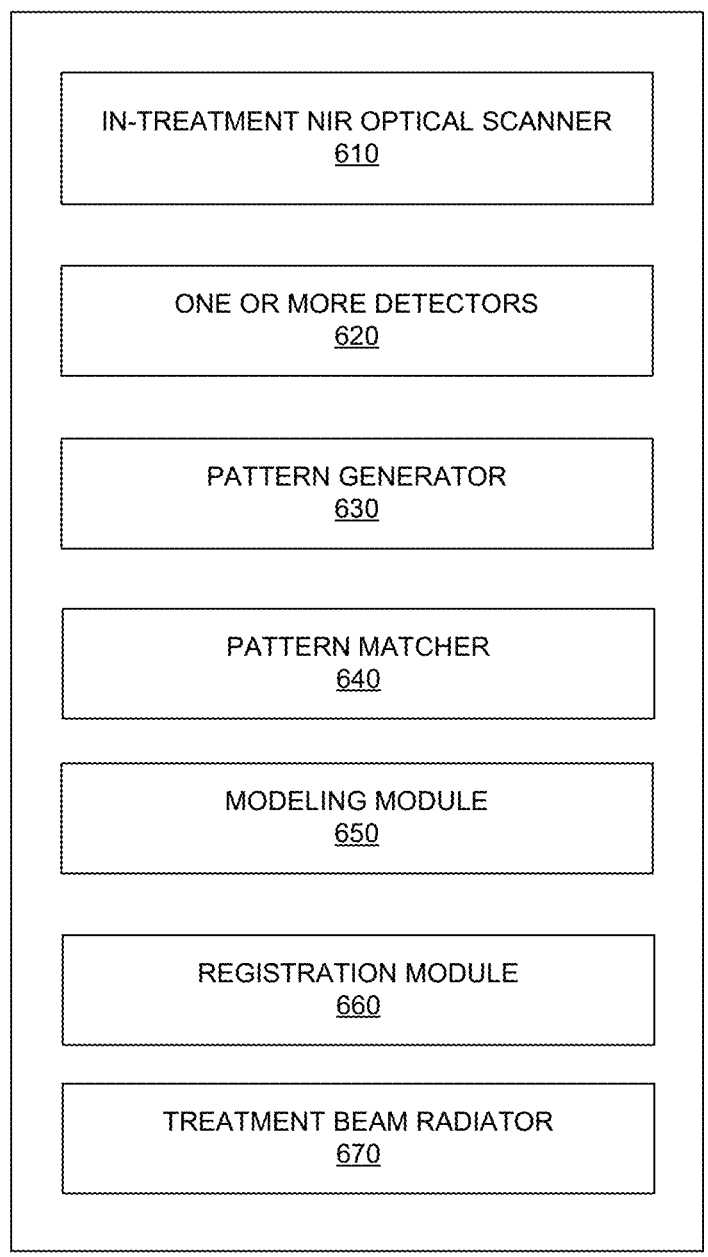
FIG. 6 is a block diagram of a system for treatment that is capable of determining skin thickness using NIR imaging for purposes of 3D positioning of a skeletal anatomy of an object, in accordance with one embodiment of the present disclosure.

FIG. 6 is a block diagram of a system 600 for treatment that is capable of determining skin thickness using NIR imaging for purposes of 3D positioning of a skeletal anatomy of an object, in accordance with one embodiment of the present disclosure. For instance, treatment system 600 is configurable to implement the method of FIGS. 5 and 15 to provide real-time determination of skin thicknesses.

In particular, system 600 includes an in-treatment NIR optical scanner 610 configured for exposing a first point on an outer surface of an object and/or patient to NIR energy from an NIR energy source. For instance, the first point comprises a beam incident point to which the energy id directed.

System 600 also includes at least one detector 620 for measuring reflected energy emanating near the first 3D point. Specifically, the detector is configured to measure the total energy radiating around the beam incident point, wherein the energy comprises energy reflecting off of the surface of the skin, various layers of the skin, and bone of the object.

System 600 also includes a pattern generator 630 for determining a pattern of the reflected energy based on a distance from a center of the reflected energy, wherein the center is approximated by the first 3D point. As will be described in relation to FIG. 12, energy is measured for each concentric ring surrounding the beam incident point. A pattern of intensity of the reflected energy is thus generated.

System 600 also includes a pattern matcher 640 for determining a skin thickness measurement based on the pattern. Specifically, similar skin thicknesses will generate similar reflection patterns for a given NIR energy wavelength. In one embodiment, the NIR energy comprises a concentrated beam at a fixed wavelength that is optimized for penetrating to the bone of a patient. In another embodiment, the NIR energy comprises multiple collinear laser beams with different wavelengths and/or polarizations.

System 600 also includes a modeling module 650 that is able to generate a 3D skeletal anatomy that compensates for skin thicknesses. Specifically, a 3D dimensional point cloud of the skin surface of an object is generated from the NIR optical scanner. Once skin thickness is compensated, a 3D point cloud of the surface of the skeletal anatomy is generated and modeled. As such, the modeling module 650 is able to determine the 3D positioning of the skeletal anatomy within a treatment system.

System 600 also includes registration module 660 that is configured for registering the 3D positioning of the skeletal anatomy obtained from the in-treatment NIR optical scan and the 3D positioning of the skeletal anatomy determined from the base scan to determine relative positioning of a skeletal anatomy and/or a surgical target within the treatment system. System 600 also includes a treatment beam radiator 670 that is configured for exposing the surgical target to a treatment beam radiation originating from the treatment system.

FIGS. 7A-7D are flow charts 700A-D illustrating various methods for patient localization, wherein each of the methods are configured to locate a patient for treatment using the methodologies for determining skin thickness. This involves registering a volumetric scan of the patient (CT or MRI data used for planning, dose calculations, etc.) onto the actual patient position in real-time. In each of the methodologies optical patient localization is determined along with volume data processing, as is described below.

In general, the first step in optical patient localization is to measure the patient's position in 3D. For example, passive and active systems for this purpose are commercially available. Passive systems use one or more cameras to observe the patient. For instance, facial features are used to track the head position and provide accuracies of 1 cm translational and 3 degrees rotational. Active solutions emit light onto the patient in a defined angle and intensity. They are less affected by the environment, more reliable and accurate and are used in embodiments of the present invention. For instance, active solutions are used to generate a point cloud representing the patient's surface in 3D (e.g., from the base scan and/or from the in-treatment optical NIR scanner).

In one embodiment, an optical laser scanner uses the triangulation principle for 3D positioning. In a triangulation setup a camera observes the reflection of a laser with known position and rotation relatively to the camera center. The 3D point position can be computed from the 2D point position in the camera image and the camera-to-laser position. To capture a 3D point set there are different methods, such as, one or two moving mirrors can be used to change the angle of the laser beam and rasterize a scene over time. Also, Microsoft Kinect uses multiple laser dots at the same time and identifies them in only one camera image just by their intensity and neighborhood. Different colors or an on-off coding over time can be also used to identify different laser angles.

Alternative methods for 3D scanning use time-of-flight and phase angle measurement. Both methods measure the distance the light has travelled from the emitter onto the target and back to the detector. The time-of-flight method uses ultra-short laser pulses and counts the time between outgoing and incoming light. The phase angle approach uses intensity modulation to modulate a waveform onto the laser beam. The travelled distance is then computed by comparing the outgoing and incoming waveforms. Again, mirrors are used to change the two beam angles and observe a full 3d scene.

The above solutions have different depth and angle resolutions and different measurement ranges. The solutions may be affected by noise, or the emitted light may interact with the skin and cause triangulation errors. For instance, one error seen during point acquisition is the elasticity of the skin, wherein the skin thickness changes depending on blood pressure, tension, temperature and due to facial expressions. Embodiments of the present invention are able to compensate for skin thickness when determining 3d positioning of the skeletal anatomy, as will be described below.

The second step is to extract the corresponding features from volumetric data. This step introduces errors, such as, in CT scans when the soft tissue contrast is low. Skin boundaries at the forehead are blurred and small changes in the threshold lead to skin thicknesses of +−1 millimeters during segmentation. Furthermore, filtering leads to intensity accumulation, meaning that in bright regions (e.g. proximity to bones) intensities are shifted towards the maximum intensity. On the other hand, bones feature high Hounsfield units and are easy to extract from CT data. Embodiments of the present invention are able to extract features as identifiable by certain skin thickness patterns, or other intensity measurement patterns (e.g., due to blood vessels or variation in the underlying material or skin).

In the third step the two feature sets are matched onto each other. That is, features determined from in-treatment optical scanning are compared to features determined from the base scan. Feature information is instrumental in obtaining accurate translational and rotational alignment. The result of this registration is the transformation between volume data and the actual patient position. Registration involves using gradient-descending algorithms (e.g., iterative closest point, "ICP") are used to iteratively match the point clouds after an initial position guess.

FIGS. 7A-D provide for the capability to optically measure additional skin properties (e.g., skin thickness) that are used to enhance triangulation and registration with the measured information. In embodiments, the skin thickness is the most significant feature to measure.

Figure 7A:
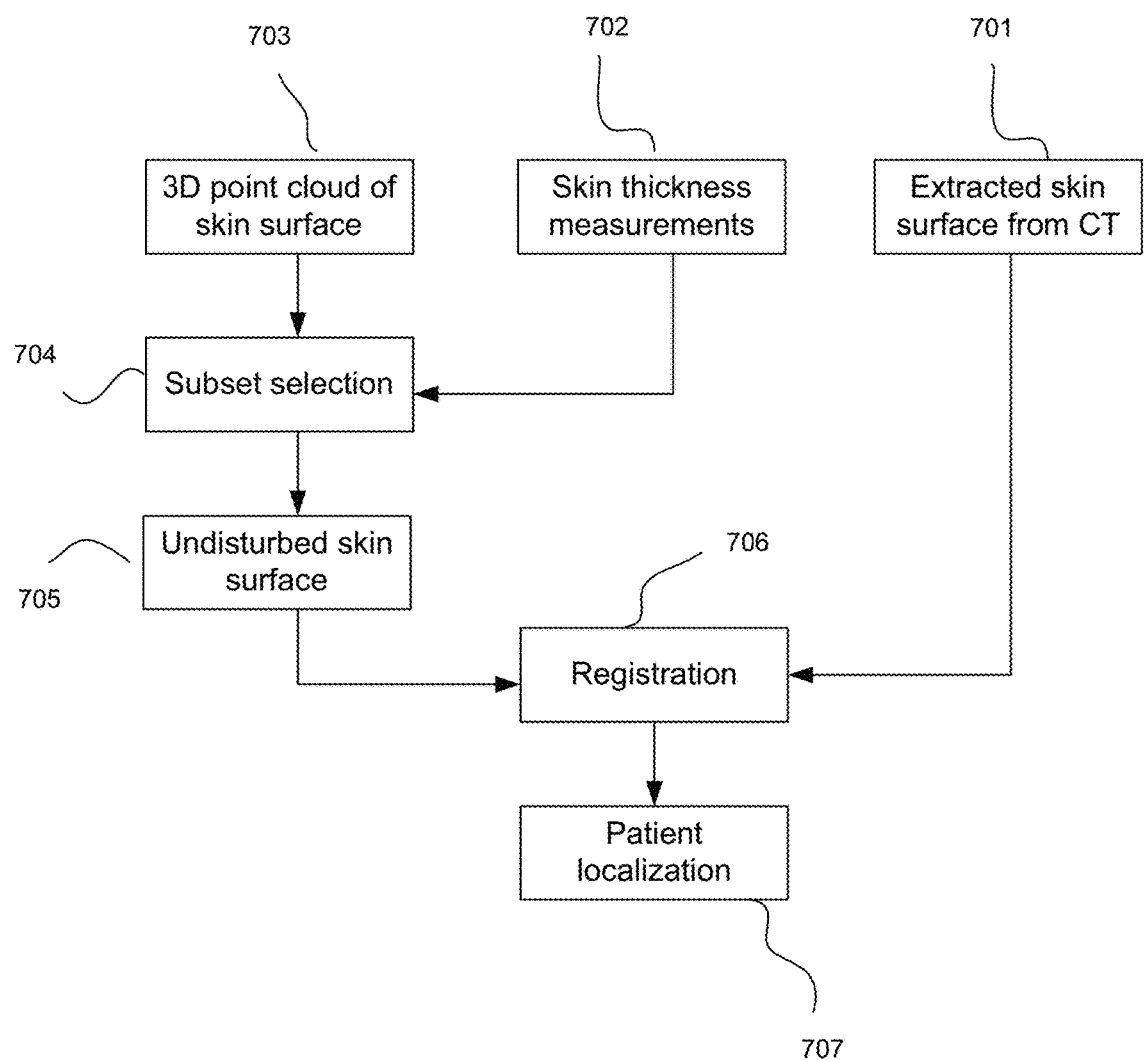
FIG. 7A is a flow diagram illustrating a method for patient localization that disregards thickness measurements not meeting a threshold when determining 3D positioning of a skeletal anatomy of an object, in accordance with one embodiment of the present disclosure.

FIG. 7A is a flow diagram 700A illustrating a method for patient localization that disregards thickness measurements not meeting a threshold when determining 3D positioning of an object, in accordance with one embodiment of the present disclosure. In a conservative approach, elastic skin deformation is handled by concentrating on areas with low skin thickness. That is, 3D points with skin thicknesses exceeding a threshold are discarded and not used for point cloud matching. Note that for this application the skin thickness measurement is reduced to simple high/low detection.

In particular, FIG. 7A concerns surface matching. A surface is optically measured using a normal laser scanner. Skin thickness is then roughly computed for all surface point. For instance, the skin thickness may be partitioned into "thick" or "thin" and nothing else. A subset of all surface points is defined so that all points in the subset have skin thickness measurements below a threshold (e.g., where the skin is thin). All points with high skin thickness are discarded. Another surface is also extracted from a planning-CT, or patient dataset. This surface and the resulting subset of skin thickens measurements is aligned for patient localization. Here the skeletal information is not computed, but the optical and CT surfaces can be aligned where skin is thin.

As shown in FIG. 7A, at 701, the skin surface is extracted from a base CT scan. Furthermore, the CT scan is able to model a 3D skeletal anatomy and to position a surgical target within the 3D skeletal anatomy.

At 703, an in-treatment NIR optical scan is performed. As such, a 3D point cloud of the skin surface is determined giving the position of the skin surface of the patient within the treatment system. In addition, rough skin thickness measurements are determined at 702. This is an attempt to determine a quality of the measurements of the 3D point cloud. For skin thicknesses exceeding a threshold, measurements for those points are discarded, thus resulting in a subset selection of measured points 704. At 705, an undisturbed skin surface is generated using the subset selection of points.

At 706, registration is performed using the skin surface information. That is, the 3D model of the skin surface obtained from the in-treatment optical scan is registered with the 3D skin surface obtained from the CT scan. As a result, alignment between the two surfaces is achieved so that the surgical target is positioned within the treatment system.

Figure 7B:
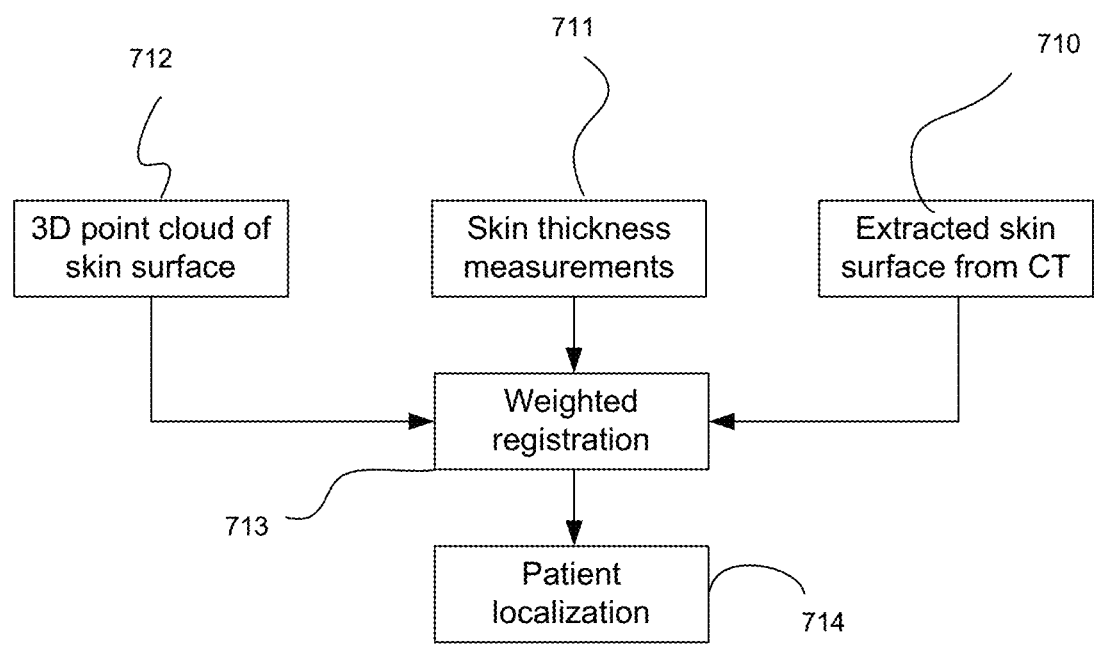
FIG. 7B is a flow diagram illustrating a method for patient localization that determines the quality of the registration between 3D skeletal models derived from a base scan and from an in-treatment optical scan using NIR imaging, in accordance with one embodiment of the present disclosure.

FIG. 7B is a flow diagram 700B illustrating a method for patient localization that determines the quality of the registration between 3D skeletal models derived from a base scan and from an in-treatment optical scan using NIR imaging, in accordance with one embodiment of the present disclosure. Using real skin thickness measurements enhances registration by determining the quality of the registration through a weighting process.

In particular, common point cloud matching algorithms calculate the distance error between point pairs in both point clouds. The sum of all distances then gives the matching quality, which is then be minimized through virtual movement of the patient in relation to the treatment system. The process shown in FIG. 7B also calculates a skin thickness error as an additional factor to the distance error of point pairs. As such, points with high skin thickness may be less weighted in the optimization process. In this way errors in regions with deformation may be tolerated or compensated for while regions with less expected deformation are accurately matched.

As shown, at 710, the skin surface is extracted from a base CT scan. Furthermore, the CT scan is able to model a 3D anatomy and to position a surgical target within the 3D anatomy. Also, a rough skin thickness measurement is determined that is sufficient for determining a skin thickness error.

At 712, an in-treatment NIR optical scan is performed. As such, a 3D point cloud of the skin surface is determined giving the position of the skin surface of the patient within the treatment system. In addition, skin thickness measurements are determined at 711, wherein a skin thickness is determined for each measured point in the point cloud. At 713, a weighted registration is performed, wherein the point clouds are registered and aligned, and a weighted quality or error factor is determined for the registration. The error factor determines the distance between point cloud pairs. It can be weighted with respect to the skin thickness measurement so that regions with low skin thickness are accented in the error sum and deformed regions are suppressed during registration. Alternatively, the skin thickness error for each point cloud pair can be added on top of the distance error to optimize for both of them. The accumulated error gives a quality of the registration, such that in an iterative process, the goal is to reduce the accumulated error to a minimum value. Once the minimum value is reached, patient localization at 714 is realized. That is, the 3D model of the skin surface of the patient is localized or positioned within the treatment system. As such, the surgical target is also localized within the treatment system.

Figure 7C:
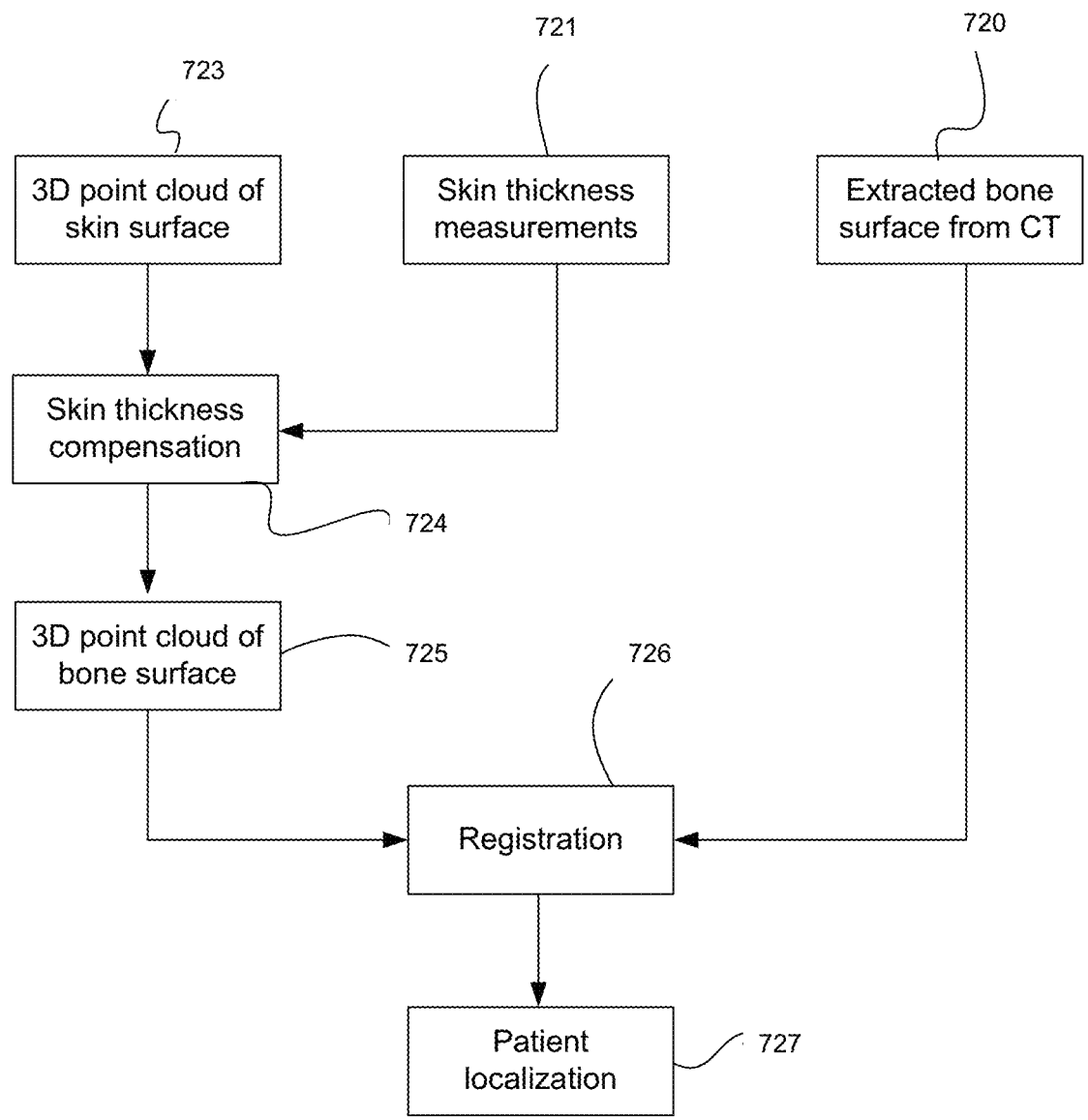
FIG. 7C is a flow diagram illustrating a method for patient localization that compensates for skin thickness when determining a 3D skeletal model derived from an in-treatment optical scan using NIR imaging, in accordance with one embodiment of the present disclosure.

FIG. 7C is a flow diagram 700C illustrating a method for patient localization that compensates for skin thickness when determining a 3D skeletal model derived from an in-treatment optical scan using NIR imaging, in accordance with one embodiment of the present disclosure. At 720, a bone surface is extracted from a base CT scan. That is, the CT scan is able to model a 3D skeletal anatomy and to position a surgical target within the 3D skeletal anatomy.

At 723, an in-treatment NIR optical scan is performed. As such, a 3D point cloud of the skin surface is determined giving the position of the skin surface of the patient within the treatment system. In addition, skin thickness measurements are determined at 721, wherein a skin thickness is determined for each measured point in the point cloud.

As stated above, skin elasticity is not the only source of errors. The skin surface is also very hard to extract from CT data. As such, skin thickness is used to compensate for any deformation in skin from one scan to another. At 724, skin thickness is compensated for in the 3D point cloud of the skin surface. That is, at each point the point cloud, the skin thickness is determined and then subtracted to give the position of the underlying bone structure. As such, at 725, a 3D point cloud of the bone surface or skeletal anatomy is determined. In particular, the measured skin thicknesses are added onto the 3D point positions in normal vector direction of the skin surface. This roughly computes the 3D surface of the underlying bone. On the other hand, the skull surface instead of the skin is extracted from the CT volume, which is very stable due to the high Hounsfield values and sharp edges of bone tissue. At 726, both point clouds are registered onto each other for patient localization. For example, registration is performed by optimally fitting the geometric shape of the two point clouds onto each other. Patient localization at 727 is realized. That is, the 3D model of the skeletal surface of the patient is localized or positioned within the treatment system. As such, the surgical target is also localized within the treatment system.

Figure 7D:
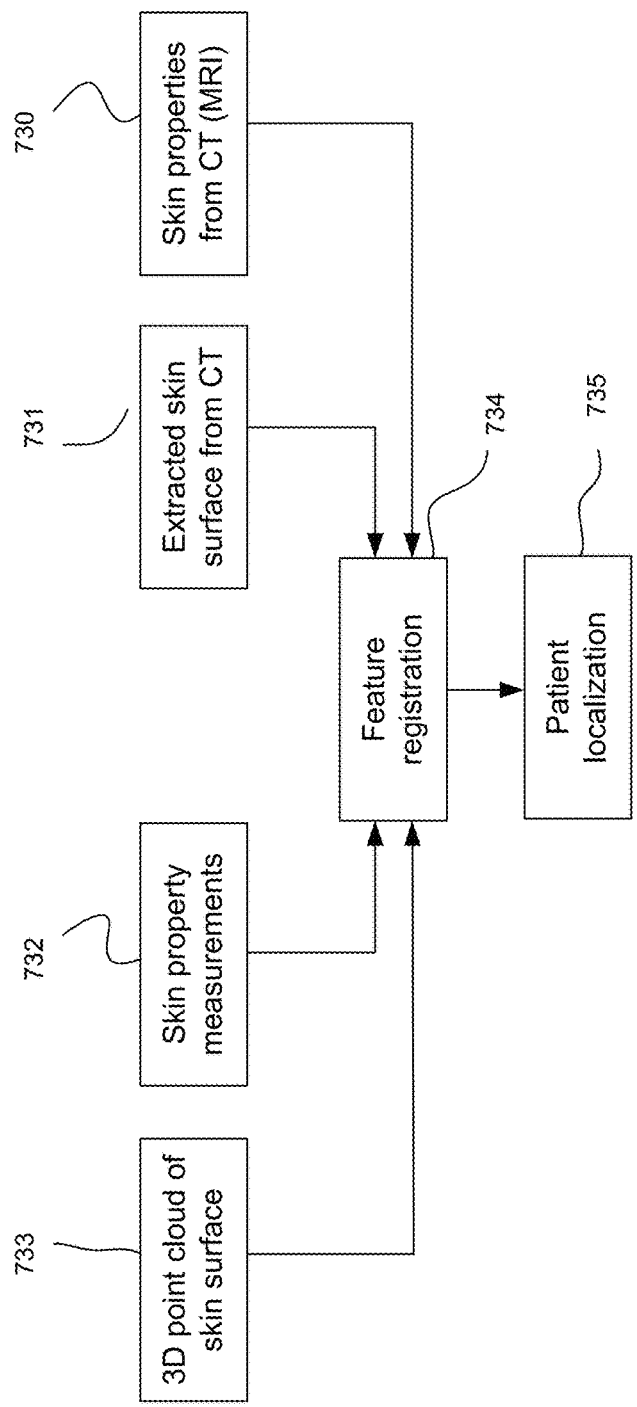
FIG. 7D is a flow diagram illustrating a method for patient localization that compensates for skin thickness when determining a 3D skeletal model derived from an in-treatment optical scan using NIR imaging, and further provides for feature registration when registering 3D skeletal models derived from a base scan and from an in-treatment optical scan using NIR imaging, in accordance with one embodiment of the present disclosure.

FIG. 7D is a flow diagram illustrating a method for patient localization that compensates for skin thickness when determining a 3D surface model derived from an in-treatment optical scan using NIR imaging, and further provides for feature registration when registering 3D surface models derived from a base scan and from an in-treatment optical scan using NIR imaging, in accordance with one embodiment of the present disclosure. Other registration techniques are supported, such as, registration algorithms focusing on feature registration instead of distance minimization. These algorithms are much faster and more precise. One example is photo stitching, where two images are registered onto each other just by mapping significant image features onto each other. As a result, head tracking is achieved through feature matching in embodiments of the present invention, where significant measured skin properties are matched with extracted skin properties from CT or MRI data. For example, regions with equal skin thickness or significant skin inhomogeneities could be matched onto each other.

At 730 and 731, a bone surface is extracted from a base CT scan. That is, the CT scan is able to model a 3D skeletal anatomy and to position a surgical target within the 3D skeletal anatomy. In addition, feature characterization is performed, such that identifiable features are discovered.

At 733, an in-treatment NIR optical scan is performed. As such, a 3D point cloud of the skin surface is determined giving the position of the skin surface of the patient within the treatment system. In addition, skin thickness measurements are determined at 732, wherein a skin thickness is determined for each measured point in the point cloud. Further, at 732, feature measurements are determined. That is, particular features are identified.

At 734, registration is performed. The registration process includes registration of skeletal anatomy point clouds for patient localization. For example, registration is performed by optimally fitting the geometric shape of the two point clouds onto each other. Additionally or alternatively, feature registration is performed to obtain more accurate alignment and registration (e.g., translational and rotational alignment) between the two point clouds. As such, patient localization at 735 is realized. That is, the 3D model of the skeletal surface of the patient is localized or positioned within the treatment system. As such, the surgical target is also localized within the treatment system.

Figure 8:
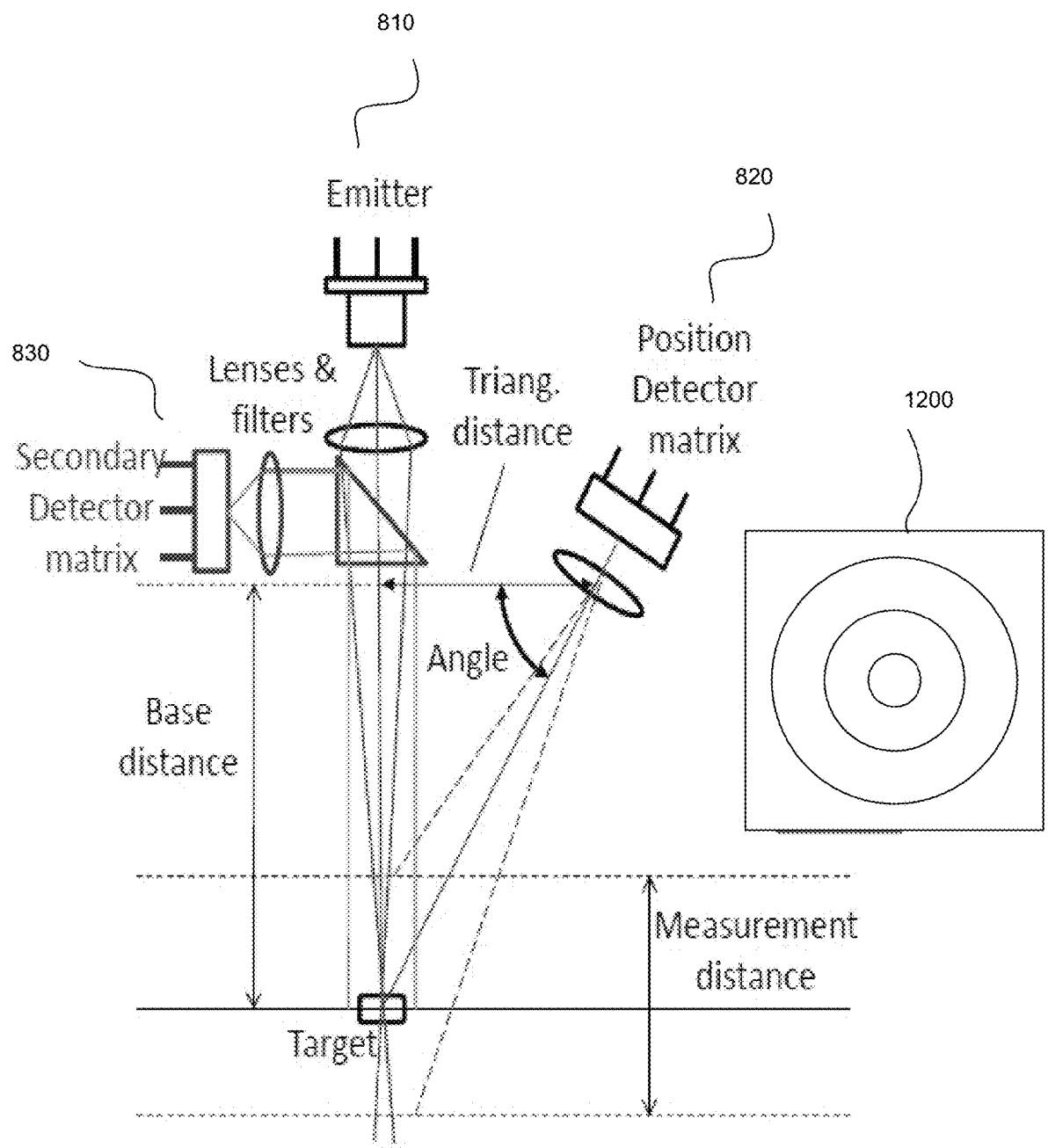
FIG. 8 is a diagram of an in-treatment optical scanning system, in accordance with one embodiment of the present disclosure.

FIG. 8 is a diagram of an in-treatment optical scanning system 800, in accordance with one embodiment of the present disclosure. In particular, backscatter analysis is used for performing skin thickness measurement. As shown, system 800 relies on a triangulation setup. A laser beam from an emitter 810 is directed onto (scanned across) a target and observed by a triangulation camera 820 to get the 3D laser spot position.

A second camera/detector 830 is equipped with a magnetic lens and aligned into the beam path using a beam splitter. In this way, detector 830 can capture high-resolution images of the laser spot wherever the laser beam is reflected by mirrors, e.g., a two axes galvanometer device which moves the beam across the target. Alternatively, a high resolution triangulation camera could be used to observe the laser spot instead of the second camera, which would also involve performing segmentation and perspective correction as preprocessing steps. As shown, seven bins 1200 are used for image analysis, however, more or a lesser amount of sensors would is also supported. For example, seven ccd line sensors or seven photodiodes would be sufficient to observe these features.

Figure 9:
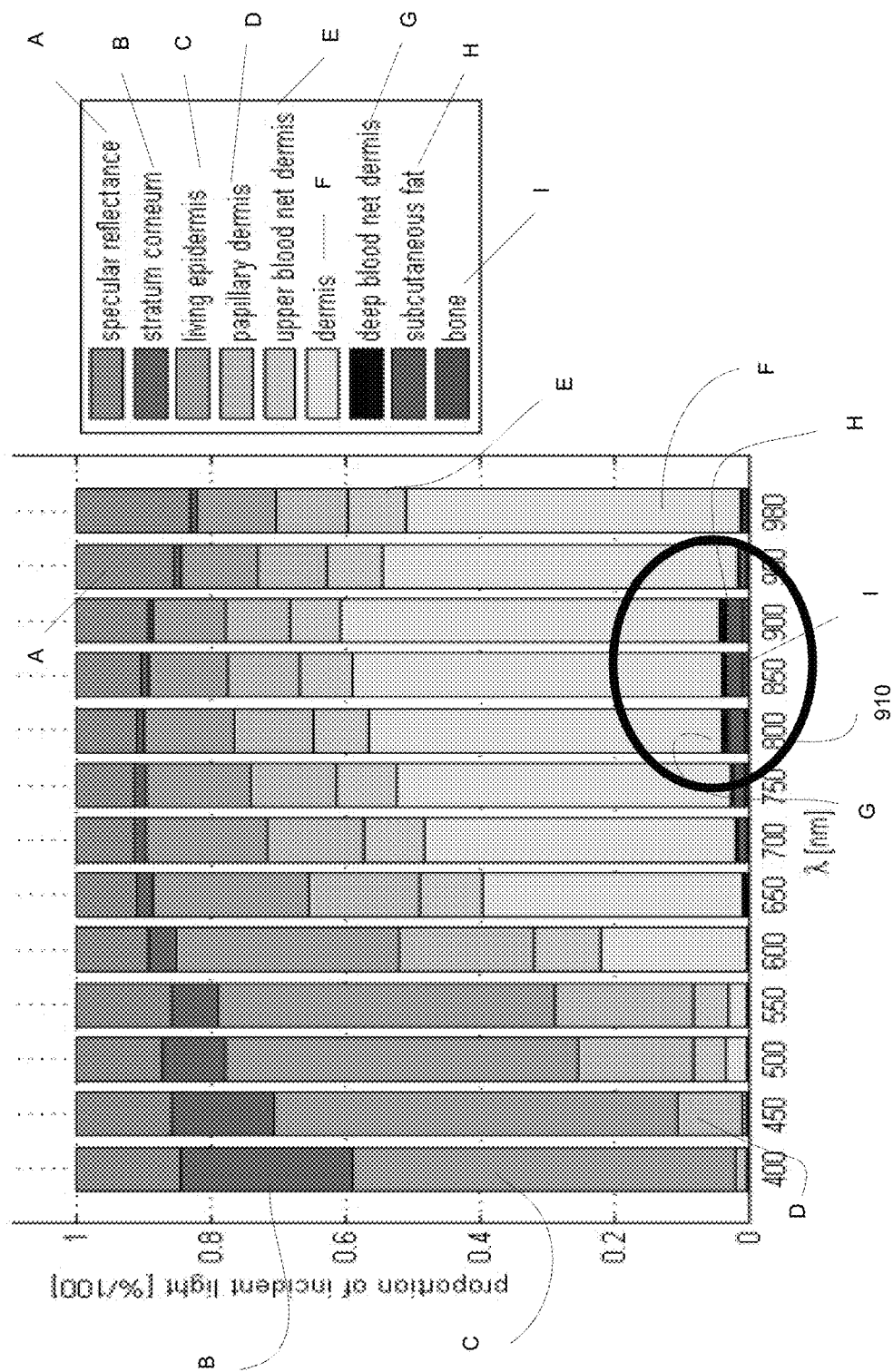
FIG. 9 is a graph illustrating the proportion of incident energy returned in relation to the thickness of the skin, in accordance with one embodiment of the present disclosure.

FIG. 9 is a graph 900 illustrating the proportion of incident energy returned in relation to the thickness of the skin, in accordance with one embodiment of the present disclosure. To find the best measurement method light propagation in skin was simulated. Embodiments of the present invention assume an eight layer skin model with mean optical properties. For instance, the eight layers include a specular reflectance (layer A), a stratum corneum (layer B), a living epidermis (layer C), a papillary dermis (layer D), an upper blood net dermis (layer E), a dermis (layer F), a deep blood net dermis (layer G), and a subcutaneous fat (layer H). A bony layer is shown as layer I. A laser beam of $2*10^8$ photons forming a Gaussian profile was directed onto the tissue. Since the skin model was generated using a defined set of parameters, the simulations allow for a precise ground truth of the desired measurements.

First, an optimal wavelength for skin penetration was chosen. The proportion of photon energy reflected from each of the eighth layers relative to the total diffuse reflection from skin surface for a selected number of wavelengths is shown below. The objective is to get as much light into deeper skin regions and back as possible. Roughly approximating photon-skin interaction light absorption increases with increasing wavelength, and scattering decreases with increasing wavelengths. As shown in FIG. 9, the optimum wavelength to use is concentrated around 800-900 nm. That is, as skin thickness information can only be found in photons from the two deepest layers, the amount of those photons has to be maximized, as is shown in circle 910. This is reached with laser wavelengths from 800-900 nm. Throughout the specification, a wavelength of 850 nm is selected by way of illustration as a primary wavelength.

Figure 10A:
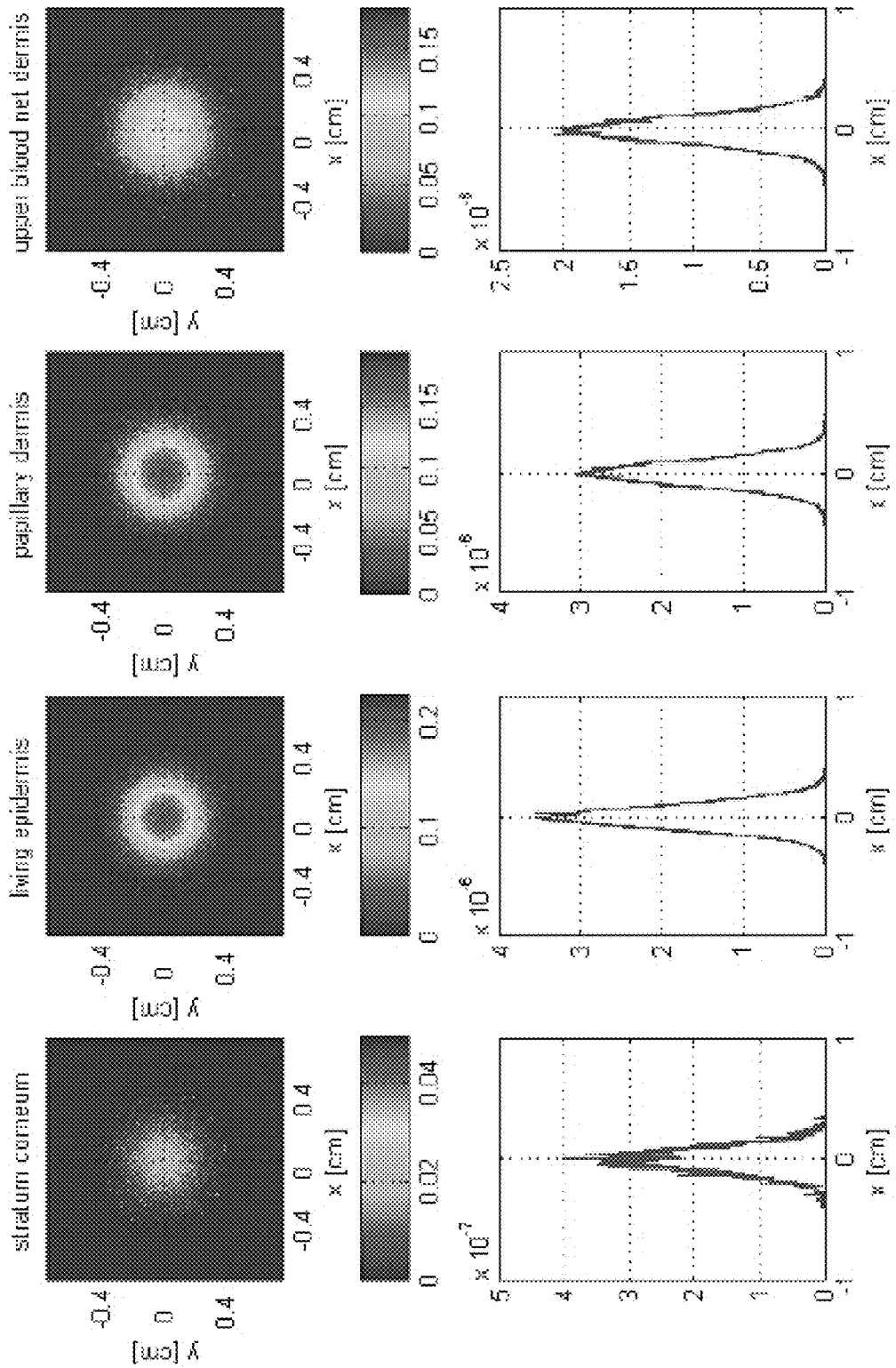
FIGS. 10A-B are multiple plots illustrating the presence of photon energy furthest away from a center for greater skin thicknesses, beam incident point, in accordance with one embodiment of the present disclosure.
Figure 10B:
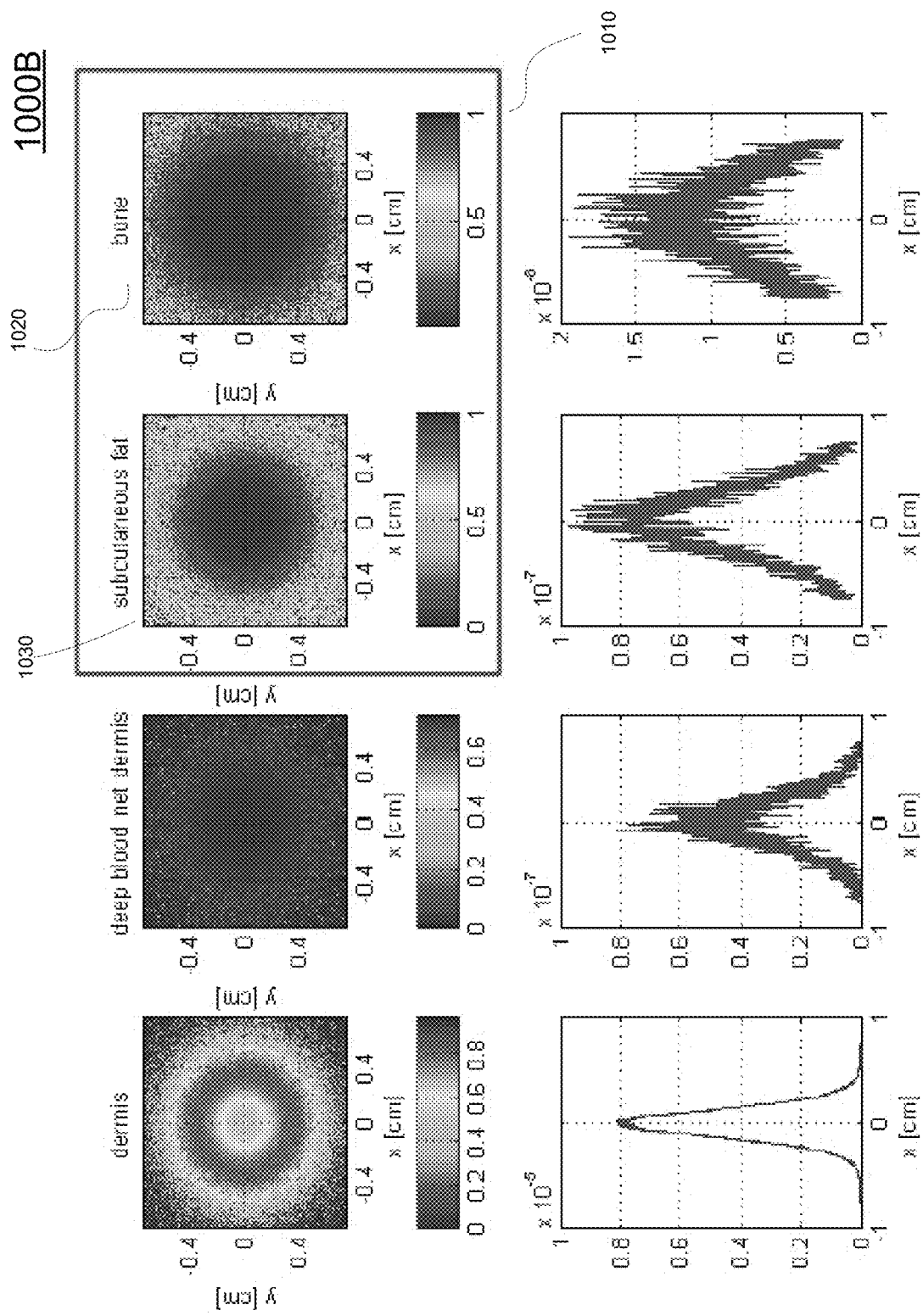

FIGS. 10A-B are multiple plots 1000 illustrating the presence of photon energy furthest away from a center for greater skin thicknesses, beam incident point, in accordance with one embodiment of the present disclosure. As shown, the spatial distribution of the backscatter is highly interesting in that the total diffuse reflection is spatially decomposed into components from each individual layer. Each location indicates the photon energy relative to the total diffuse reflection in this location. It is observed that at higher distances from the beam center the percentage of photons from deep lasers increase. For instance, as is shown in highlighted area 1010, reflectance energy of deep layers of subcutaneous fat is shown out to a larger radii from a center, beam incident point in plot 1030. Also, reflectance of bone is shown out to an even larger radii in plot 1020 than that for the subcutaneous fat layer. A good tradeoff between percentage and photon count can be found at distances of 4 to 7 millimeters from the center, beam incident point.

Figure 10C:
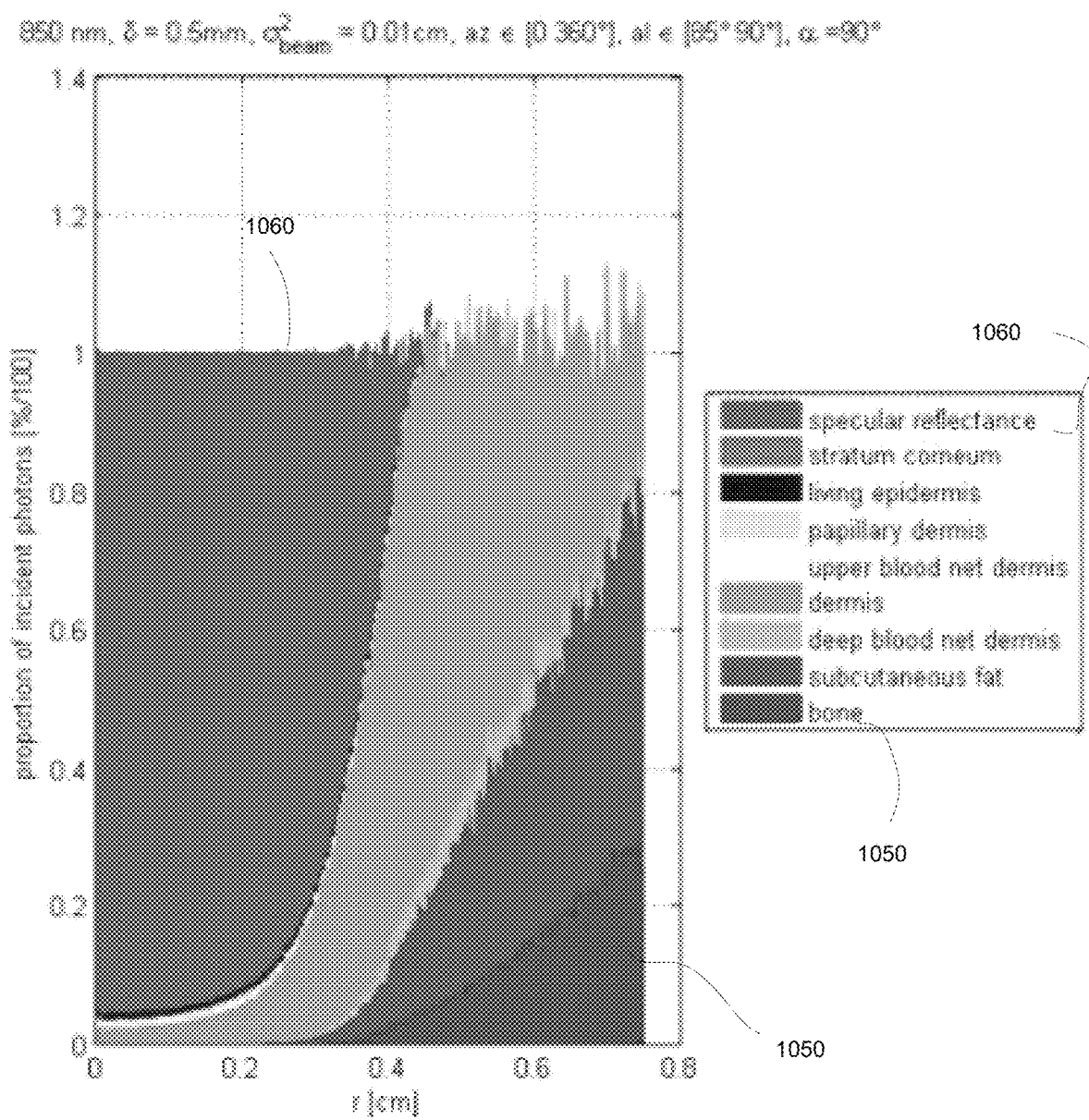
FIG. 10C is a graph showing presence of photon energy at various radii from a beam incident point, in accordance with one embodiment of the present disclosure.

FIG. 10C is a graph 1000C showing presence of photon energy at various radii from a beam incident point, in accordance with one embodiment of the present disclosure. For instance, photon energy due to the contribution of specular reflectance 1060 is present out to a radius of approximately 4 mm. Deeper layers, such as, a bone 1050 have a reflectance photon energy out to radius greater than approximately 8 mm.

Figure 11:
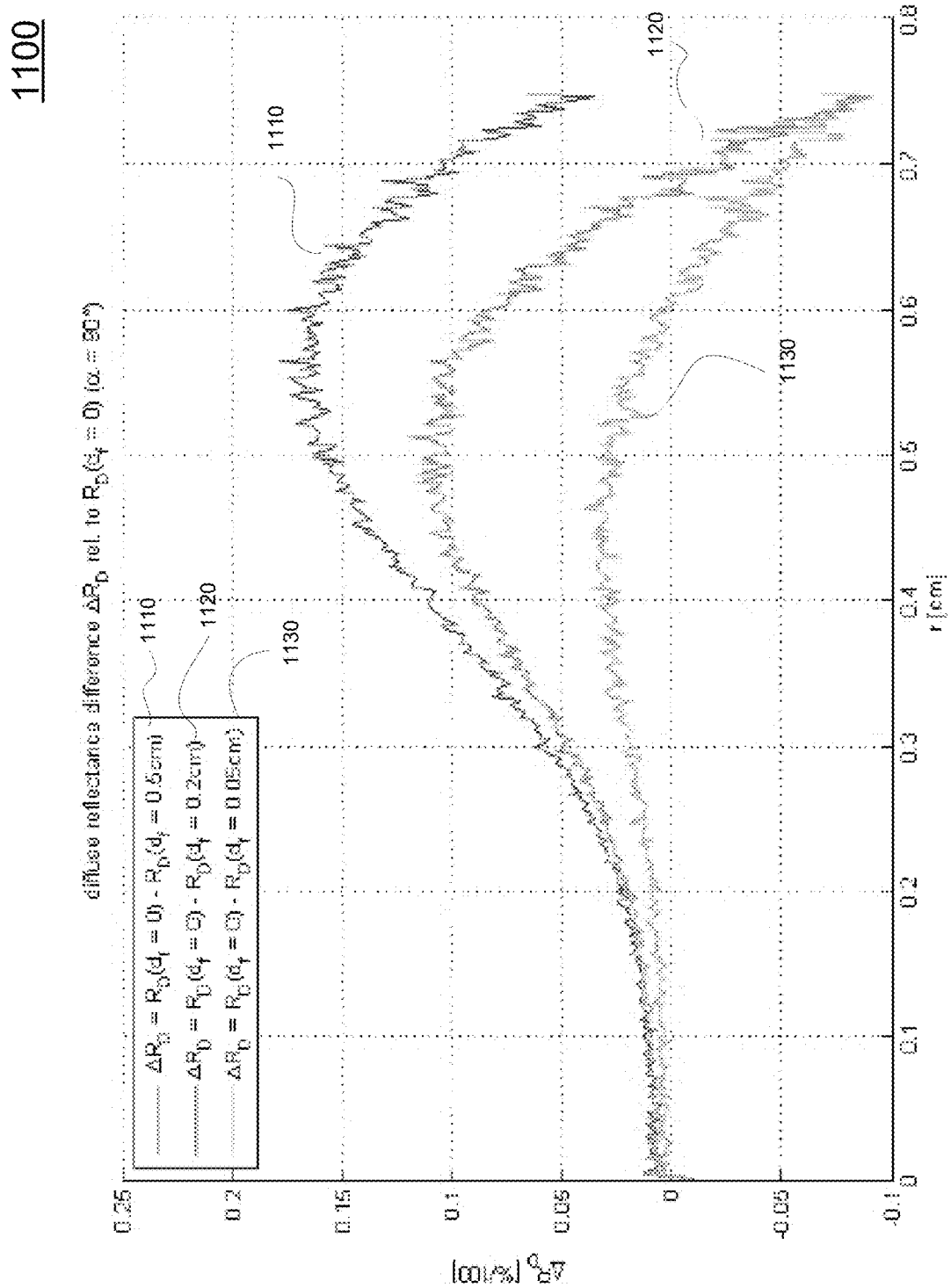
FIG. 11 is a chart illustrating a pattern of incident energy spread over radii from a center, beam incident point for various skin thicknesses, in accordance with one embodiment of the present disclosure.

FIG. 11 is a chart 1100 illustrating a pattern of incident energy spread over radii from a center, beam incident point for various skin thicknesses, in accordance with one embodiment of the present disclosure. As shown, the highest amount of intensity changes for different skin thicknesses can be found in the regions around of 4 to 7 millimeters from the center, beam incident point. The relative intensity changes for skin thicknesses of 3 mm to 8 mm are given below. For instance, measurement 1110 corresponding to a skin thickness of 5 mm, measurement 1120 corresponds to a skin thickness of 2 mm, and measurement 1130 corresponds to a skin thickness of 0.5 mm.

Each of the measurements show varying intensities at the different radii away from the center, beam incident point. For example, at 5 millimeters radius an intensity increase of 10 percent from 3 to 5 millimeters (fat from 0 to 2 mm) can be seen. This value could be used for skin thickness measurement.

Figure 12:
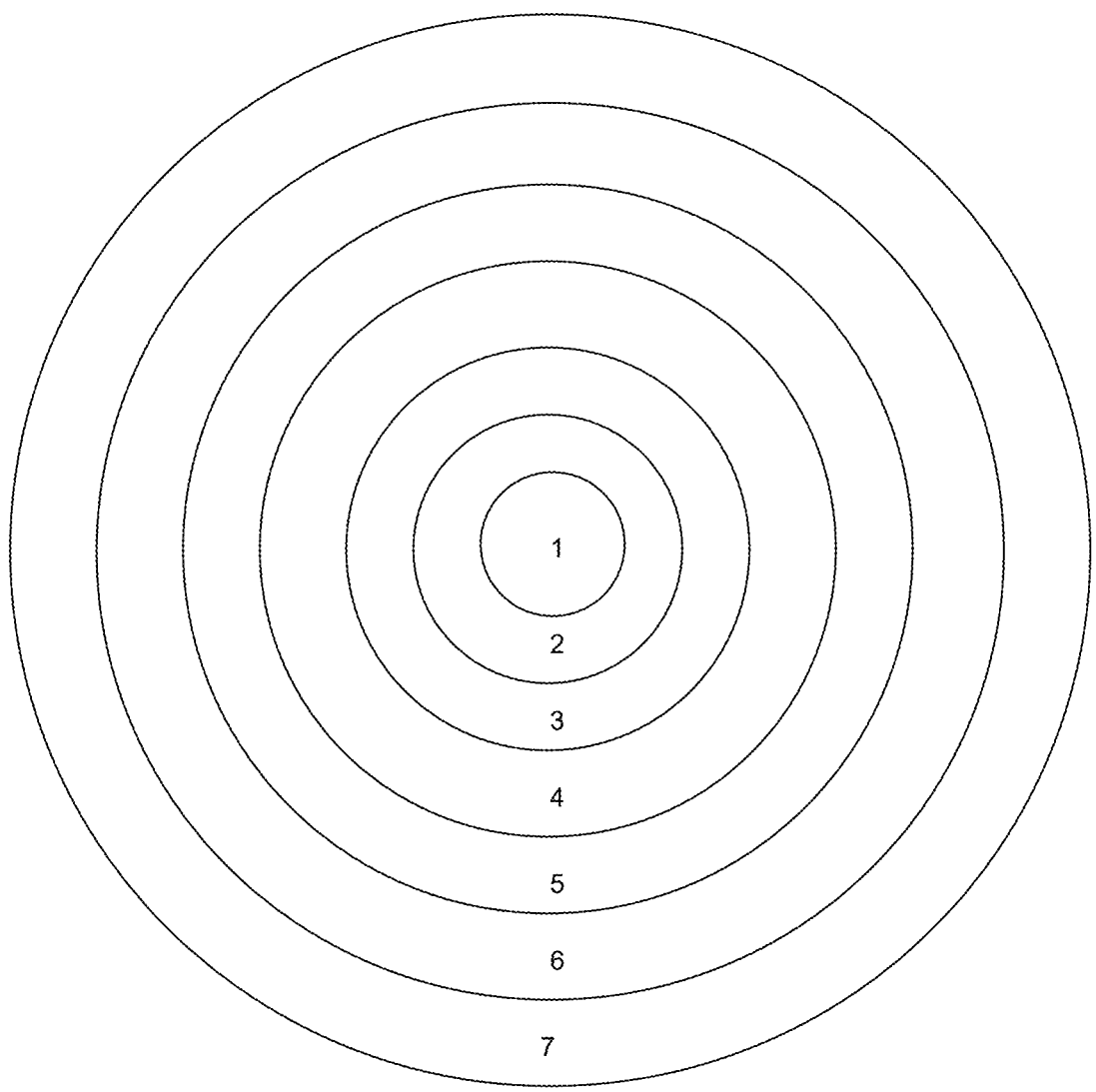
FIG. 12 is a diagram illustrating a plurality of concentric rings about a center, beam incident point, within which photon energy is detected when measuring skin thickness, in accordance with one embodiment of the present disclosure.

In another embodiment, to achieve higher accuracy, additional features have been selected for skin thickness measurement. FIG. 12 is a diagram 1200 illustrating a plurality of concentric rings about a center, beam incident point, within which photon energy is detected when measuring skin thickness, in accordance with one embodiment of the present disclosure. Concentric regions (1-7) of interest were defined around the beam center with 1 mm width. For each region, the total energy (sum of pixel intensities) is accumulated (e.g., for noise rejection).

Figure 13:
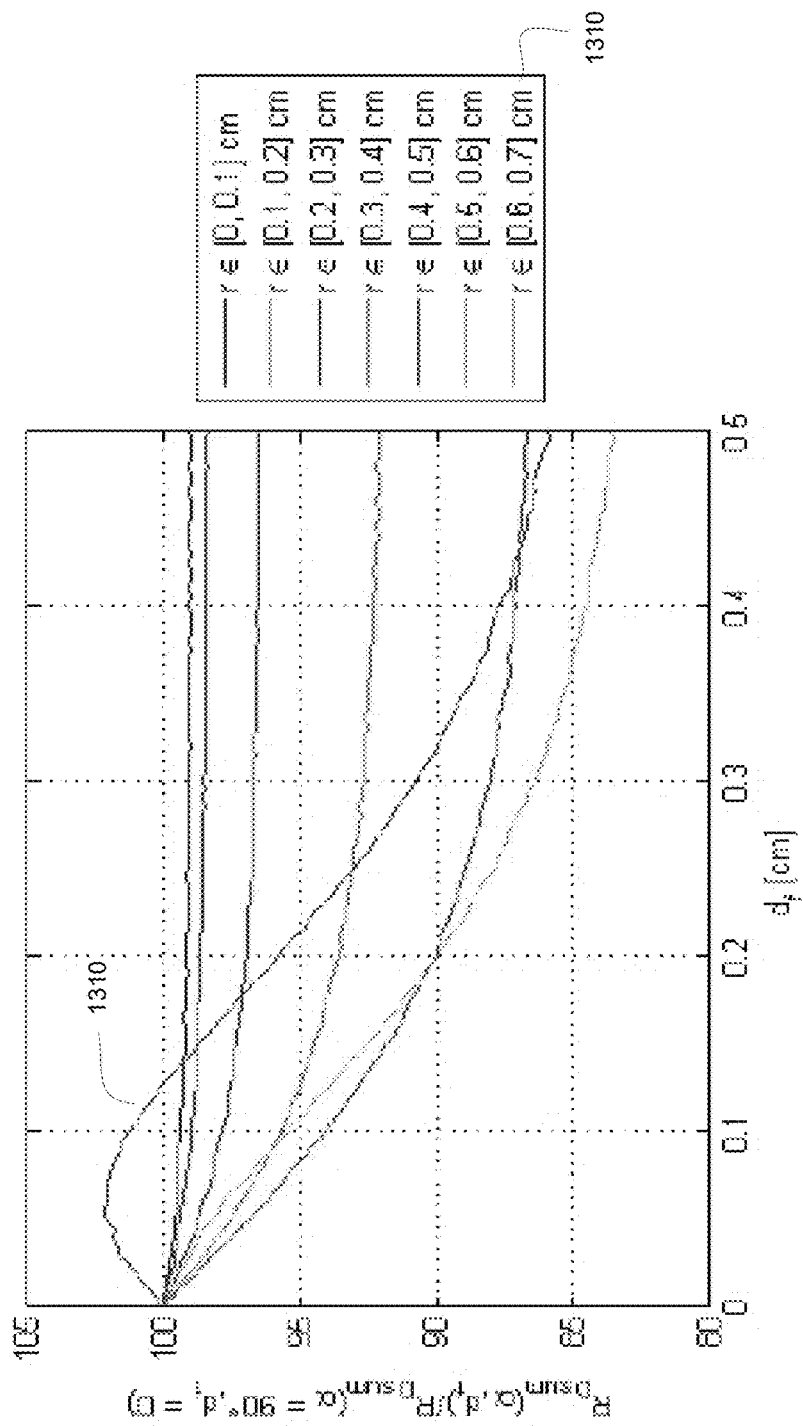
FIG. 13 is a chart illustrating the dependencies between skin thickness and region intensity, in accordance with one embodiment of the present disclosure.

FIG. 13 is a chart illustrating the dependencies between skin thickness and region intensity, in accordance with one embodiment of the present disclosure. For instance, chart 1300 illustrates the feature measurements for various skin thicknesses under a first set of parameters. As shown in chart 1300, the largest skin thicknesses shown by line 1310 show a non-linear response for prominent feature characterization. This is compared to more linear responses for thinner skin thicknesses, showing no features.

Figure 14A:
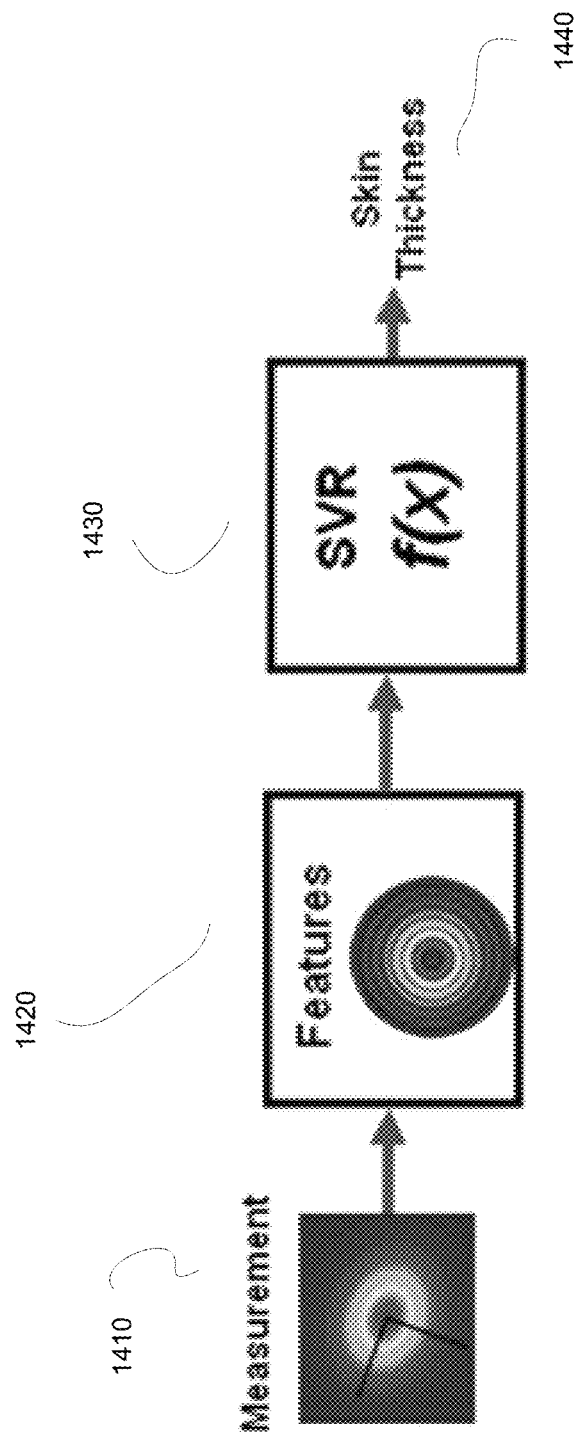
FIG. 14A is an illustration of the calculation of skin thickness, in accordance with one embodiment of the present disclosure.

FIG. 14 is an illustration of the calculation of skin thickness, in accordance with one embodiment of the present disclosure. In particular, at 1410 measurements are taken using traditional scanning techniques (e.g., CT, MRI, etc.), as well as using in-treatment optical scanners (e.g., NIR scanning). Features are determined at 1420 for both the base scan and the in-treatment optical scan. At 1430, using state-of-the-art prediction algorithms such as Support Vector Regression (SVR) trained on these features, this allows for the inference of the thickness of the fat layer and thus the whole skin from the camera image at 1440. Additionally, using SVR and image preprocessing error sources, varying intensities and non-orthogonal beam incident angle can be also handled.

Figure 14B:
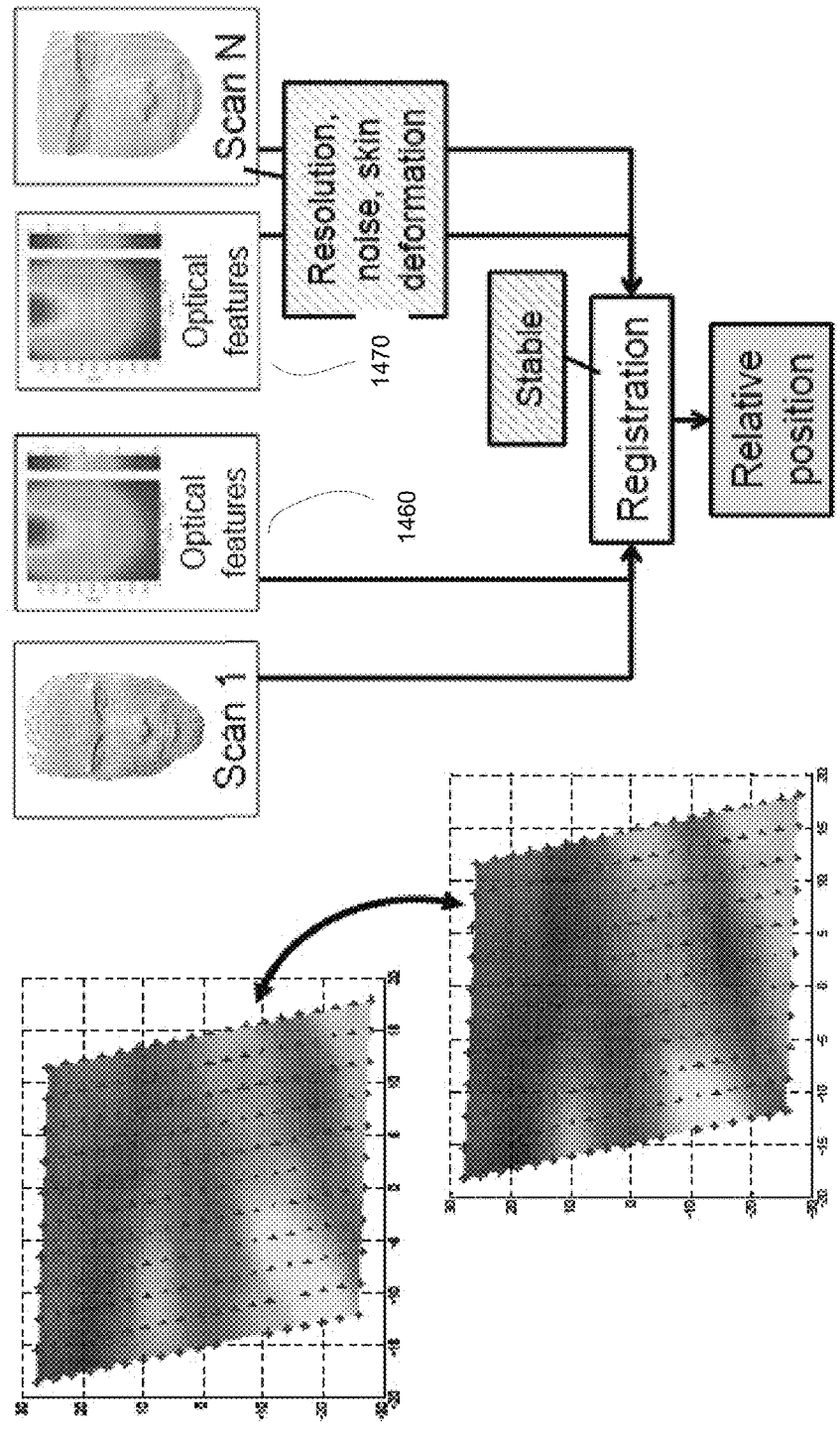
FIG. 14B is a flow chart illustrating the use of feature labeled point cloud registration on a continuous basis, for purposes of patient localization, in accordance with one embodiment of the present disclosure.

FIG. 14B is a flow chart illustrating the use of feature labeled point cloud registration on a continuous basis, for purposes of patient localization, in accordance with one embodiment of the present disclosure. As shown, feature measurement is performed and is used for registering a point cloud derived from a base scan (e.g., planning-CT scan) and a point cloud derived from an in-treatment optical scanner (e.g., NIR energy source). Without incorporating features, registration may be insufficient when considering rotational positioning, since the object may have a consistent shape across different rotational positions. However, incorporating features into the registration process increases the accuracy in rotational positioning, as the features have an exact position about a rotational axis. For instance, optical features measured from scan 1 in plot 1460 is similar to the optical features measured in scan N in plot 1470, and presumably for any scan between scans 1 and scan N. As a result, performing registration for a 3D surface model derived in scan N against the 3D surface model derived in scan 1 is stable. The resulting relative positioning of the 3D surface model for scan N, as well as the corresponding surgical target, within the treatment system is therefore obtained with higher accuracy.

Figure 15:
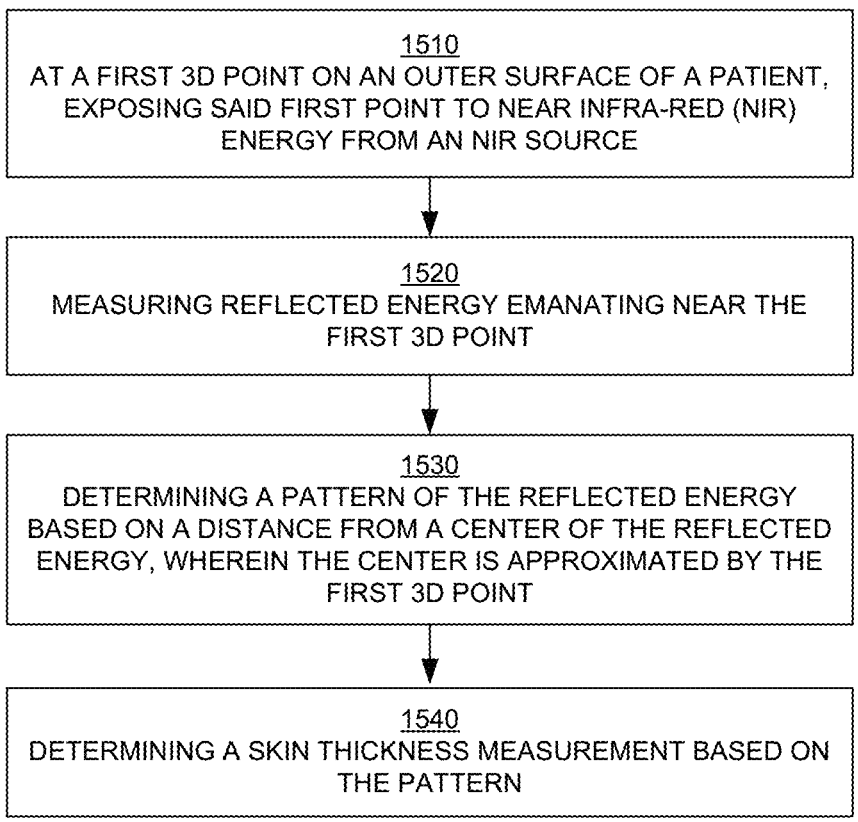
FIG. 15 is a flow chart illustrating a method for determining skin thickness using NIR imaging, in accordance with one embodiment of the present disclosure.

FIG. 15 is a flow chart 1500 illustrating a method for determining skin thickness using NIR imaging, in accordance with one embodiment of the present disclosure. Some or all of the operations in flow diagram 1500 are performed within a computing system including a processor and memory coupled to the processor and having stored therein instructions that, if executed by the computer system cause the system to execute a method for determining skin thickness using NIR imaging. In still another embodiment, instructions for performing a method are stored on a non-transitory computer-readable storage medium having computer-executable instructions causing a computer system to perform a method for determining skin thickness using NIR imaging. The method outlined in flow diagram 1500 is implementable by one or more of the components of the computer system 100 and system 600 of FIG. 6, and system 800 of FIG. 8.

At 1510, at a first 3D point on an outer surface of a patient, the method includes exposing the first point to near infra-red (NIR) energy from an NIR source. For example, the energy comprises a concentrated beam at a fixed wavelength (e.g., 700-950 nm), in one embodiment. In another embodiment, the NIR energy comprises multiple collinear laser beams comprising a combination of various wavelengths and/or polarizations.

At 1520, the method includes measuring reflected energy emanating near the first 3D point. At 1530, the method includes determining a pattern of the reflected energy based on a distance from a center of the reflected energy approximated by the first 3D point (e.g., the center, beam incident point). For example, in one embodiment, this includes defining a plurality of concentric rings around the first 3D point. A reflected photon accumulated count is determined for each of the plurality of concentric rings. A photon accumulated count plot is generated for the plurality of concentric rings to generate the pattern.

At 1540, the method includes determining a skin thickness measurement based on the pattern. Specifically, this includes comparing the generated pattern of photon accumulated counts against a plurality of predefined patterns reflecting thicknesses of skin. The method includes matching the generated pattern of photon accumulated counts to one of the plurality of predefined patterns, and assigning a skin thickness measurement to the first 3D point based on a matched predefined pattern. Further, the method considers the angle between the incoming laser beam and the skin surface to compensate for measurement errors. The angle is determined from the 3D information of the surrounding 3D points. Further, statistical information about the particular patient (e.g., skin type, color) may also be computed from a full dataset of NIR information or obtained from other sources.

In one embodiment, a set of numerical values representing photon counts is computed, and a mathematical model is used to compute skin thickness. In particular, a detector is used to capture reflected light of a laser spot. In the case of 2D cameras, the measured intensities/photon counts are accumulated for certain areas to obtain the numerical features. Additional measurement information is collected, such as, the angle between the laser and the surface, the distance to the target, etc. A mathematical model is used to transform measurement and feature data into a skin thickness value. In one implementation, the mathematical model is generated using various methodologies that consider statistical data. For instance, support vector regression (SVR) is used for the mathematical model in one implementation, which is a learning algorithm that operates similar to neuronal networks. It can be trained to provide a set of input/output pairs, and is configurable to determine a corresponding function. That is, SVR modeling can be trained to consider different skin tones, blood pressures, sweat, and laser angles, such that the best possible function is determined that considers all the input data. Further, SVR modeling can be patient specific, such that the SVR modeling can be trained for a particular patient, which results in better performance. For instance, by classifying skin tone prior to treatment, the accuracy of the SVR modeling is increased. Therefore, the inclusion of statistical data is useful.

Figure 16:
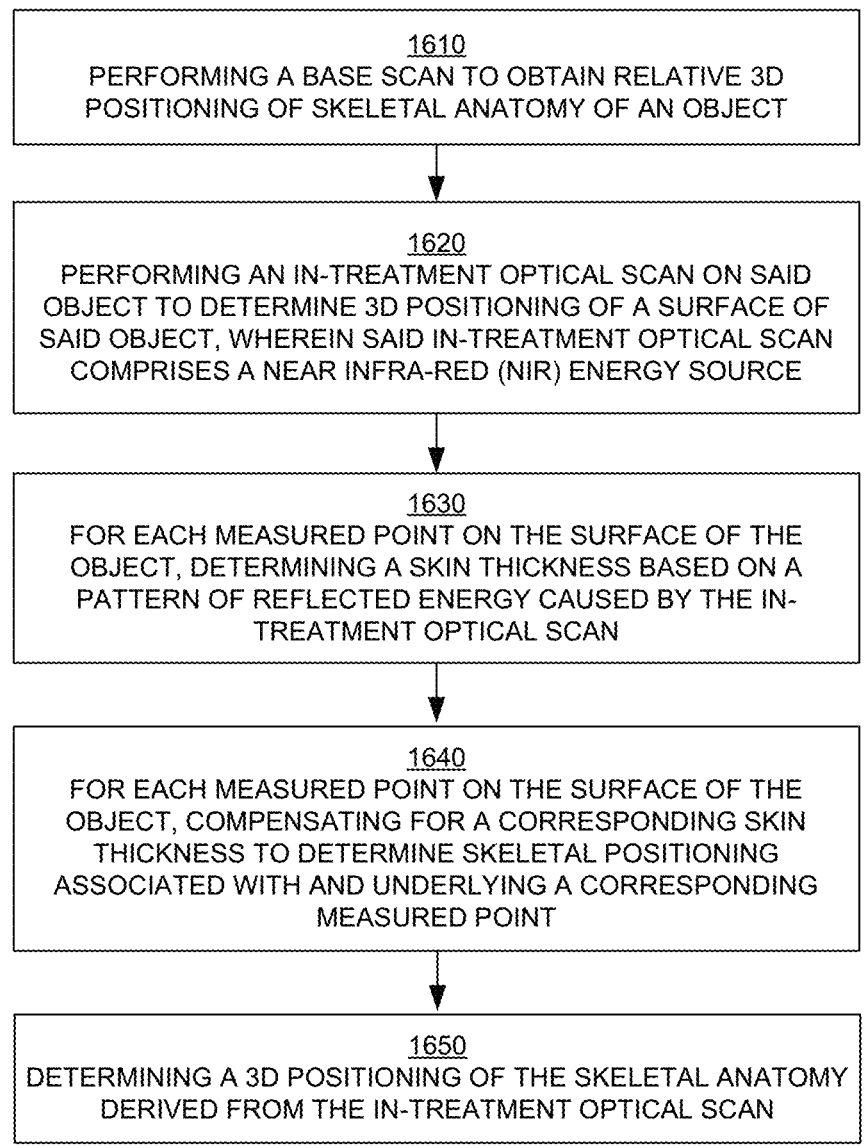
FIG. 16 is a flow chart illustrating a method for determining skin thickness using NIR imaging for purposes of 3D positioning of a skeletal anatomy of an object, in accordance with one embodiment of the present disclosure.

FIG. 16 is a flow chart illustrating a method for determining skin thickness using NIR imaging for purposes of 3D positioning of a skeletal anatomy of an object, in accordance with one embodiment of the present disclosure. Some or all of the operations in flow diagram 1600 are performed within a computing system including a processor and memory coupled to the processor and having stored therein instructions that, if executed by the computer system cause the system to execute a method for determining skin thickness using NIR imaging for purposes of 3D positioning of a skeletal anatomy of an object. In still another embodiment, instructions for performing a method are stored on a non-transitory computer-readable storage medium having computer-executable instructions causing a computer system to perform a method for determining skin thickness using NIR imaging for purposes of 3D positioning of a skeletal anatomy of an object. The method outlined in flow diagram 1600 is implementable by one or more of the components of the computer system 100 and system 600 of FIG. 6, and system 800 of FIG. 8.

At 1610, the method includes performing a base scan to obtain relative 3D positioning of skeletal anatomy of an object. For instance, an MRI or CT scan (e.g., a planning scan) may be taken to obtain the positioning information for the skeletal anatomy. In addition, the base scan is able to obtain relative 3D positioning of a surgical target within the skeletal anatomy.

At 1620, the method includes performing an in-treatment optical scan on the object to determine 3D positioning of a surface of the object, wherein the in-treatment optical scan comprises a near infra-red (NIR) energy source. That is, using techniques outlined in embodiments of the present invention, a 3D model of the surface to the object is obtained.

At 1630, for each measured point on the surface of the object, the method includes determining a skin thickness based on a pattern of reflected energy caused by the in-treatment optical scan. For example, skin thickness is determined by exposing each measured point to NIR energy. Then, at each measured point, the method includes defining a plurality of concentric rings around the first 3D point. Further, at each measured point, a reflected photon accumulated count is determined for each of the plurality of concentric rings. Also, at each measured point, the method includes plotting photon accumulated counts for each of the plurality of concentric rings to generate the pattern. At each measured point, the generated pattern of photon accumulated counts is compared against a plurality of predefined patterns reflecting thicknesses of skin. At each measured point, the generated pattern of photon accumulated counts is matched to one of the plurality of predefined patterns. Finally, at each measured point, a skin thickness measurement is assigned to the first 3D point based on a matched predefined pattern.

At 1640, for each measured point on the surface of said object, the method includes compensating for a corresponding skin thickness to determine skeletal positioning associated with and underlying a corresponding measured point. For example, compensation includes subtracting a corresponding skin thickness from a corresponding 3D surface positioning measurement to determine the skeletal positioning corresponding to a corresponding measured point, as previously described.

At 1650, the method includes determining a 3D positioning of the skeletal anatomy derived from the in-treatment optical scan. That is, a skeletal model of the patient is generated that is positioned within a coordinate system of a treatment system.

The method includes registering the 3D positioning of the skeletal anatomy derived from the in-treatment optical scan and the 3D positioning of said skeletal anatomy derived from the base scan to determine relative positioning of the surgical target within the treatment system.

Additionally, registration may include feature registration. That is, a first identifiable feature is determined on the surface of said object derived from the base scan, wherein said identifiable feature comprises an associated location on the skeletal anatomy derived from the base scan. Also, a second identifiable feature is determined on the surface of the object derived from the in-treatment optical scan, wherein the second identifiable feature comprises an associated location on the skeletal anatomy derived from the in-treatment optical scan. The second identifiable feature may be determined from skin thickness or related patterns of reflected signals from measured points associated the feature. The first and second identifiable features are matched based on common characteristics.

Further, registration of the 3D positioning of the skeletal anatomy derived from said in-treatment optical scan and said 3D positioning of the skeletal anatomy derived from the base scan is performed using the alignment between the first and second identifiable features. In particular, feature registration includes determining translational and rotational alignment between both 3D positioning of corresponding skeletal anatomies.

Because no ionizing radiation is being used during the localization process, the process of determining skeletal and therefore target position can be continuous, in embodiments of the present invention. For example, the method includes performing the in-treatment optical scan on the object on a periodic basis. The method includes updating registration of the 3D positioning of the skeletal anatomy derived from the in-treatment optical scan and the 3D positioning of the skeletal anatomy derived from the base scan based on a current in-treatment optical scan to determine current relative positioning of the surgical target within the treatment system. Thereafter, the surgical target and a treatment beam radiation are aligned based on the current relative positioning to expose the surgical target to the treatment beam radiation.

Thus, according to embodiments of the present disclosure, systems and methods are described providing for patient modeling and localization using NIR imaging. In other embodiments, systems and methods are described for determining skin thickness to determine skeletal positioning of an object using NIR imaging.

While the foregoing disclosure sets forth various embodiments using specific block diagrams, flowcharts, and examples, each block diagram component, flowchart step, operation, and/or component described and/or illustrated herein may be implemented, individually and/or collectively, using a wide range of hardware, software, or firmware (or any combination thereof) configurations. In addition, any disclosure of components contained within other components should be considered as examples because many other architectures can be implemented to achieve the same functionality.

The process parameters and sequence of steps described and/or illustrated herein are given by way of example only and can be varied as desired. For example, while the steps illustrated and/or described herein may be shown or discussed in a particular order, these steps do not necessarily need to be performed in the order illustrated or discussed. The various example methods described and/or illustrated herein may also omit one or more of the steps described or illustrated herein or include additional steps in addition to those disclosed.

While various embodiments have been described and/or illustrated herein in the context of fully functional computing systems, one or more of these example embodiments may be distributed as a program product in a variety of forms, regardless of the particular type of computer-readable media used to actually carry out the distribution. The embodiments disclosed herein may also be implemented using software modules that perform certain tasks. These software modules may include script, batch, or other executable files that may be stored on a computer-readable storage medium or in a computing system. These software modules may configure a computing system to perform one or more of the example embodiments disclosed herein. One or more of the software modules disclosed herein may be implemented in a cloud computing environment. Cloud computing environments may provide various services and applications via the Internet. These cloud-based services (e.g., software as a service, platform as a service, infrastructure as a service, etc.) may be accessible through a Web browser or other remote interface. Various functions described herein may be provided through a remote desktop environment or any other cloud-based computing environment.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the invention and its practical applications, to thereby enable others skilled in the art to best utilize the invention and various embodiments with various modifications as may be suited to the particular use contemplated.

Embodiments according to the present disclosure are thus described. While the present disclosure has been described in particular embodiments, it should be appreciated that the disclosure should not be construed as limited by such embodiments.

What is claimed:

1. A system, comprising:
   a processor; and
   memory coupled to the processor, the memory having instructions stored therein that, when executed, cause the system to perform a method comprising:
   receiving and measuring reflected energy from a patient at a detector device, the reflected energy from reflection of a beam of near infrared (NIR) energy by the patient's skin at a first point of the patient's skin;
   generating a pattern of the reflected energy based on a distance from the first point;
   determining a thickness measurement of the patient's skin at the first point based on the pattern;
   repeating said receiving, said measuring, said generating, and said determining for a plurality of additional points on the outer surface of the patient's skin other than the first point, to determine a plurality of thickness measurements that includes the thickness measurement at the first point;
   determining points of a bone surface of the patient using at least a subset of the thickness measurements;
   determining a position of a target in the patient with respect to the bone surface; and
   determining an alignment for a beam of radiation that aligns the beam of radiation with the target.

2. The system of claim 1, wherein the NIR energy has a fixed wavelength.

3. The system of claim 1, wherein the beam of NIR energy comprises multiple collinear laser beams comprising a combination of various wavelengths and various polarizations.

4. The system of claim 1, wherein said generating a pattern comprises, for each point on the outer surface of the patient's skin including the first point:
   defining a respective plurality of concentric rings around said each point;
   determining a respective reflected photon accumulated count for each said respective plurality of concentric rings; and
   plotting the respective photon accumulated count for each said respective plurality of concentric rings to generate the pattern for the each point.

5. The system of claim 4, wherein said determining a thickness measurement comprises, for said each point:
   comparing the pattern for said each point against a plurality of predefined patterns reflecting thicknesses of skin;
   matching the pattern for said each point to a predefined pattern of the plurality of predefined patterns; and
   assigning a thickness measurement associated with the predefined pattern to said each point.

6. The system of claim 1, wherein said using at least a subset of the thickness measurements comprises:
   generating a three-dimensional (3D) point cloud of the skin surface based on said repeating;
   generating a 3D point cloud of the patient's skeletal anatomy using the points of the bone structure and the subset of the thickness measurements; and
   registering the 3D point cloud of the patient's skeletal anatomy with a 3D positioning of the skeletal anatomy obtained from a base scan of the patient.

7. A system, comprising:
   a processor; and
   memory coupled to the processor, the memory comprising program modules that are executable by the processor, the program modules configured to:
   measure reflected energy received at a detector device, the reflected energy from reflection of a beam of near infrared (NIR) energy by points on a surface of a patient during a first scan of the patient with the beam of NIR energy;
   for each of the points on the surface of the patient, determine a corresponding skin thickness based on a pattern of the reflected energy;
   for said each of the points on the surface of the patient, compensate for the corresponding skin thickness to determine a skeletal position associated with and underlying said each of the points;
   determine a position of skeletal anatomy of the patient derived from the skeletal positioning for said each of the points;
   determine a position of a target in the patient with respect to the position of the skeletal anatomy; and
   determine an alignment for a beam of radiation that aligns the beam of radiation with the target.

8. The system of claim 7, wherein the program modules are further configured to, for said each of the points on the surface of the patient, subtract the corresponding skin thickness to determine the skeletal position corresponding to the point.

9. The system of claim 7, wherein the program modules are further configured to obtain a relative position of the skeletal anatomy and a relative position of a target within the skeletal anatomy from a base scan performed prior to the first scan.

10. The system of claim 9, wherein the program modules are further configured to register the position of the skeletal anatomy derived from the first scan and the position of the skeletal anatomy derived from the base scan to determine the relative position of the target within the skeletal anatomy.

11. The system of claim 10, wherein the program modules are further configured to:
determine a first identifiable feature on the surface of the patient in the base scan, wherein the identifiable feature comprises an associated location on the skeletal anatomy derived from the base scan;
determine a second identifiable feature on the surface of the patient derived from the first scan, wherein the second identifiable feature comprises an associated location on the skeletal anatomy derived from the first scan;
match the first and second identifiable features based on common characteristics; and
register the position of the skeletal anatomy derived from the first scan and the position of the skeletal anatomy derived from the base scan using the alignment between the first and second identifiable features.

12. The system of claim 11, wherein the program modules are further configured to determine the second identifiable feature based on related skin thicknesses or related patterns of reflected signals from points associated with the second identifiable feature.

13. The system of claim 11, wherein the program modules are further configured to determine rotational alignment between the position of the skeletal anatomy derived from the first scan and the position of the skeletal anatomy derived from the base scan.

14. The system of claim 7, wherein the program modules are further configured to, for said each of the points:
define a plurality of concentric rings around the point;
determine a reflected photon accumulated count for each of the concentric rings;
plot photon accumulated counts for each of the concentric rings to generate the pattern;
compare the pattern of against a plurality of predefined patterns reflecting thicknesses of skin;
match the pattern to a predefined pattern of the plurality of predefined patterns; and
assign a thickness measurement associated with the pattern to the point.

15. A system, comprising:
a detector operable for receiving and measuring reflected energies, the reflected energies from reflection of a beam of near infrared (NIR) energy, from an NIR source, by a patient's skin at each point of a plurality of points on the patient's skin exposed to the beam by an optical scanner; and
a computer system coupled to the detector and operable for performing operations comprising:
determining patterns comprising a pattern of each reflected energy of the reflected energies based on a distance from a respective point of the points;
determining thickness measurements comprising a thickness measurement of the patient's skin at said each point of the points based on the pattern around said each point;
determining points of a bone surface of the patient using at least a subset of the thickness measurements; and
determining a position of a target in the patient with respect to the bone surface.

16. The system of claim 15, wherein the detector is aligned with the beam's paths to capture the reflected energies around beam incident points, wherein the points on the outer surface of the patient's skin comprise the beam incident points.

17. The system of claim 15, wherein the NIR energy has a fixed wavelength.

18. The system of claim 15, wherein the operations further comprise:
defining a respective plurality of concentric rings around said each point;
determining a respective reflected photon accumulated count for each the respective plurality of concentric rings; and
plotting the respective photon accumulated count for each the respective plurality of concentric rings to generate the patterns.

19. The system of claim 18, wherein the operations further comprise:
comparing the patterns against a plurality of predefined patterns reflecting thicknesses of skin;
matching each pattern of the patterns to a respective predefined pattern of the plurality of predefined patterns; and
assigning a thickness measurement associated with the respective predefined pattern to a respective point of the points.

* * * * *